US008688607B2

(12) United States Patent
Pacha

(10) Patent No.: US 8,688,607 B2
(45) Date of Patent: Apr. 1, 2014

(54) SYSTEM AND METHOD FOR DETECTING HEALTHCARE INSURANCE FRAUD

(76) Inventor: Debra Pacha, Oviedo, FL (US)

( * ) Notice: Subject to any disclaimer, the term of this patent is extended or adjusted under 35 U.S.C. 154(b) by 340 days.

(21) Appl. No.: 13/162,560

(22) Filed: Jun. 16, 2011

(65) Prior Publication Data

US 2011/0246229 A1    Oct. 6, 2011

Related U.S. Application Data

(63) Continuation-in-part of application No. 11/938,582, filed on Nov. 12, 2007, now abandoned.

(51) Int. Cl.
*G06F 17/00* (2006.01)
*G06N 5/00* (2006.01)

(52) U.S. Cl.
USPC .......................................................... 706/45

(58) Field of Classification Search
USPC .......................................................... 706/47
See application file for complete search history.

(56) References Cited

U.S. PATENT DOCUMENTS 8,060,394 B2 * 11/2011 Woodings et al. ........... 705/7.13
8,214,232 B2 *  7/2012 Tyler et al. ....................... 705/2

* cited by examiner

*Primary Examiner* — Michael B Holmes
(74) *Attorney, Agent, or Firm* — McKinney Law, PLLC

(57) ABSTRACT

A system and method for detecting healthcare insurance fraud is disclosed. The method includes creating a database containing source data related to at least one healthcare claim submitted for reimbursement, selecting data from the database to compare to a set of rules using an audit module, and comparing the selected data to the set of rules using the audit module. The method also includes using the audit module to automatically identify suspected fraudulent data when the selected data violates at least one rule of the set of rules and using the audit module to flag the fraudulent data. In addition, the method includes using the audit module to generate a report illustrating patterns of irregularities within the source data to visually identify the fraudulent data displayed within the source data by user-friendly graphs and charts, and generating at least one automated statement for display to identify the at least one rule of the set of rules that was violated by the selected data using a documentation module.

12 Claims, 33 Drawing Sheets

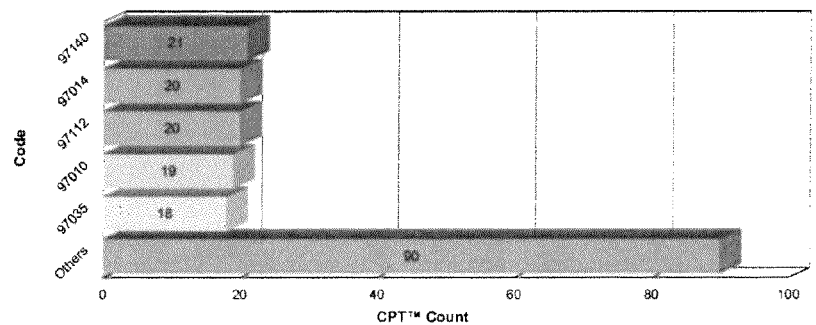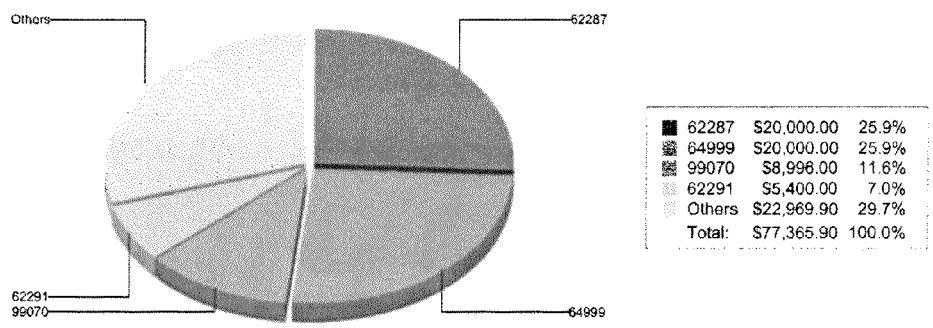
*FIG. 5a*

| Code | Modifier | Billed | Units | Description |
|---|---|---|---|---|
| 00000 | | $400.00 | 2 | DESCRIPTION NOT FOUND |
| 20552 | | $350.00 | 1 | INJECTION SINGLE/MLT TRIGGER POINT 1/2 MUSCLES |
| 62287 | | $20,000.00 | 1 | DCMPRN PERQ NUCLEUS PULPOSUS 1/> LEVELS LUMBAR |
| 62290 | | $3,750.00 | 2 | NJX DISKOGRAPY EA LVL LMBR |
| 62291 | | $5,400.00 | 2 | NJX DISKOGRAPY EA LVL CRV/THRC |
| 64999 | | $20,000.00 | 1 | UNLIS PX NRVS SYS |
| 72040 | | $155.00 | 1 | RADEX SPI CRV 2/3 VIEWS |
| 72070 | | $200.00 | 1 | RADEX SPI THRC 2 VIEWS |
| 72100 | | $150.00 | 1 | RADEX SPI LUMBOSAC 2/3 VIEWS |
| 72110 | | $250.00 | 1 | RADEX SPI LUMBOSAC MINIMUM 4 VIEWS |
| 72141 | | $1,850.00 | 1 | MRI SPI CANAL&CNTS CRV C-MATRL |
| 72148 | | $1,850.00 | 1 | MRI SPI CANAL&CNTS LMBR C-MATRL |
| 72170 | | $100.00 | 1 | RADEX PELVIS 1/2 VIEWS |
| 72285 | | $1,200.00 | 2 | DISKOGRAPY CRV/THRC RS&I |
| 72295 | | $1,200.00 | 2 | DISKOGRAPY LMBR RS&I |
| 97010 | | $855.00 | 19 | APPL MODALITY 1+ AREAS HOT/COLD PACKS |
| 97012 | | $40.00 | 1 | APPL MODALITY 1+ AREAS TRCJ MCHNL |
| 97014 | | $600.00 | 20 | APPL MODALITY 1+ AREAS ELEC STIMJ UNATTN |
| 97035 | | $540.00 | 18 | APPL MODALITY 1+ AREAS US EA 15 MIN |
| 97039 | | $30.00 | 1 | UNLIS MODALITY SPEC TYP&TM IF CONSTANT ATTN |
| 97110 | | $1,020.00 | 17 | THER PX 1+ AREAS EA 15 MIN THER XERSS |
| 97112 | | $1,200.00 | 20 | THER PX 1+ AREAS EA 15 MIN NEUROMUSC REEDUCAJ |
| 97140 | | $1,155.00 | 21 | MNL THER TQS 1+ REGIONS EA 15 MIN |
| 99024 | | $0.00 | 4 | PO F-UP VST RELATED TO ORIGINAL PX |
| 99070 | | $8,996.00 | 4 | SUPPLIES&MATERIALS PRV BY PHYS >&ABOVE |
| 99144 | | $1,000.00 | 2 | M-SEDAJ BY SM PHYS PERFRMG SVC 5+ YR |
| 99202 | | $135.00 | 1 | OFFICE OUTPT NEW 20 MINUTES |
| 99211 | | $935.00 | 17 | OFFICE O/P EST 5 MIN |
| 99212 | | $240.00 | 3 | OFFICE OUTPT EST 10 MIN |
| 99213 | 25 | $300.00 | 1 | OFFICE OUTPT EST 15 MIN |
| 99214 | | $400.00 | 1 | OFFICE OUTPT EST 25 MIN |
| 99242 | | $350.00 | 1 | OFFICE CONSLTJ 30 MIN |
| 99243 | | $375.00 | 1 | OFFICE CONSLTJ 40 MIN |
| 99244 | | $1,000.00 | 1 | OFFICE CONSLTJ 60 MIN |
| A4461 | | $200.00 | 1 | SURGICL DRESS HOLD NON-REUSE |
| E0942 | | $200.00 | 1 | CERVICAL HEAD HARNESS/HALTER |
| J0690 | | $5.70 | 2 | CEFAZOLIN SODIUM INJECTION |
| J1885 | | $11.50 | 1 | KETOROLAC TROMETHAMINE INJ |
| J2001 | | $25.00 | 1 | LIDOCAINE INJECTION |
| J2175 | | $3.70 | 2 | MEPERIDINE HYDROCHL /100 MG |
| J3301 | | $15.00 | 1 | TRIAMCINOLONE ACET INJ NOS |
| J7050 | | $20.00 | 2 | NORMAL SALINE SOLUTION INFUS |
| S9982 | | $400.00 | 2 | MED RECORD COPY PER PAGE |
| S9988 | | $459.00 | 2 | SERV PART OF PHASE I TRIAL |
| | Total | $77,365.90 | | |

FIG. 5b

SIU# 04-110005      CODE SECTION DEFINITION AND UTILIZATION
PATIENT: TEST TEST
CLAIM NUMBER: 0000
DATE OF BIRTH: 12/31/1999
DATE OF INJURY: 05/28/2007
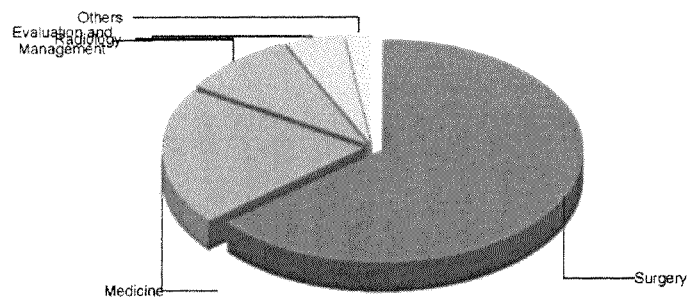
| | | | |
|---|---|---:|---:|
| ■ | Surgery | $49,500.00 | 64.0% |
| ■ | Medicine | $15,436.00 | 20.0% |
| ■ | Radiology | $6,955.00 | 9.0% |
| | Evaluation and Management | $3,735.00 | 4.8% |
| | Others | $1,739.90 | 2.2% |
| | Total: | $77,365.90 | 100.0% |
*FIG. 6a*

SIU# 04-110005                    CODE SECTION DEFINITION AND UTILIZATION

PATIENT:          TEST TEST
CLAIM NUMBER:     0000
DATE OF BIRTH:    12/31/1999
DATE OF INJURY:   05/28/2007

CPT™ Section

| Code | Modifier | Billed | Units | Description | |
|------|----------|--------|-------|-------------|---|
| NOT ASSIGNED | | | | | $400.00 |
| 00000 | | $400.00 | 2 | DESCRIPTION NOT FOUND | |
| EVALUATION AND MANAGEMENT | | | | | $3,735.00 |
| 99202 | | $135.00 | 1 | OFFICE OUTPT NEW 20 MINUTES | |
| 99211 | | $935.00 | 17 | OFFICE O/P EST 5 MIN | |
| 99212 | | $240.00 | 3 | OFFICE OUTPT EST 10 MIN | |
| 99213 | 25 | $300.00 | 1 | OFFICE OUTPT EST 15 MIN | |
| 99214 | | $400.00 | 1 | OFFICE OUTPT EST 25 MIN | |
| 99242 | | $350.00 | 1 | OFFICE CONSLTJ 30 MIN | |
| 99243 | | $375.00 | 1 | OFFICE CONSLTJ 40 MIN | |
| 99244 | | $1,000.00 | 1 | OFFICE CONSLTJ 60 MIN | |
| SURGERY | | | | | $49,500.00 |
| 20552 | | $350.00 | 1 | INJECTION SINGLE/MLT TRIGGER POINT 1/2 MUSCLES | |
| 62287 | | $20,000.00 | 1 | DCMPRN PERQ NUCLEUS PULPOSUS 1/> LEVELS LUMBAR | |
| 62290 | | $3,750.00 | 2 | NJX DISKOGRAPY EA LVL LMBR | |
| 62291 | | $5,400.00 | 2 | NJX DISKOGRAPY EA LVL CRV/THRC | |
| 64999 | | $20,000.00 | 1 | UNLIS PX NRVS SYS | |
| RADIOLOGY | | | | | $6,955.00 |
| 72040 | | $155.00 | 1 | RADEX SPI CRV 2/3 VIEWS | |
| 72070 | | $200.00 | 1 | RADEX SPI THRC 2 VIEWS | |
| 72100 | | $150.00 | 1 | RADEX SPI LUMBOSAC 2/3 VIEWS | |
| 72110 | | $250.00 | 1 | RADEX SPI LUMBOSAC MINIMUM 4 VIEWS | |
| 72141 | | $1,850.00 | 1 | MRI SPI CANAL&CNTS CRV C-MATRL | |
| 72148 | | $1,850.00 | 1 | MRI SPI CANAL&CNTS LMBR C-MATRL | |
| 72170 | | $100.00 | 1 | RADEX PELVIS 1/2 VIEWS | |
| 72285 | | $1,200.00 | 2 | DISKOGRAPHY CRV/THRC RS&I | |
| 72295 | | $1,200.00 | 2 | DISKOGRAPY LMBR RS&I | |
| MEDICINE | | | | | $15,436.00 |
| 97010 | | $855.00 | 19 | APPL MODALITY 1+ AREAS HOT/COLD PACKS | |
| 97012 | | $40.00 | 1 | APPL MODALITY 1+ AREAS TRCJ MCHNL | |
| 97014 | | $600.00 | 20 | APPL MODALITY 1+ AREAS ELEC STIMJ UNATTN | |
| 97035 | | $540.00 | 18 | APPL MODALITY 1+ AREAS US EA 15 MIN | |
| 97039 | | $30.00 | 1 | UNLIS MODALITY SPEC TYP&TM IF CONSTANT ATTN | |
| 97110 | | $1,020.00 | 17 | THER PX 1+ AREAS EA 15 MIN THER XERSS | |
| 97112 | | $1,200.00 | 20 | THER PX 1+ AREAS EA 15 MIN NEUROMUSC REEDUCAJ | |
| 97140 | | $1,155.00 | 21 | MNL THER TQS 1+ REGIONS EA 15 MIN | |
| 99024 | | $0.00 | 4 | PO F-UP VST RELATED TO ORIGINAL PX | |
| 99070 | | $8,996.00 | 4 | SUPPLIES&MATERIALS PRV BY PHYS >&ABOVE | |
| 99144 | | $1,000.00 | 2 | M-SEDAJ BY SM PHYS PERFRMG SVC 5+ YR | |
| MEDICAL AND SURGICAL SUPPLIES | | | | | $200.00 |
| A4461 | | $200.00 | 1 | SURGICL DRESS HOLD NON-REUSE | |
| DURABLE MEDICAL EQUIPMENT | | | | | $200.00 |
| E0942 | | $200.00 | 1 | CERVICAL HEAD HARNESS/HALTER | |
| DRUGS | | | | | $80.90 |
| J0690 | | $5.70 | 2 | CEFAZOLIN SODIUM INJECTION | |
| J1885 | | $11.50 | 1 | KETOROLAC TROMETHAMINE INJ | |
| J2001 | | $25.00 | 1 | LIDOCAINE INJECTION | |
| J2175 | | $3.70 | 2 | MEPERIDINE HYDROCHL /100 MG | |
| J3301 | | $15.00 | 1 | TRIAMCINOLONE ACET INJ NOS | |
| J7050 | | $20.00 | 2 | NORMAL SALINE SOLUTION INFUS | |
| TEMPORARY NATIONAL CODES | | | | | $859.00 |
| S9982 | | $400.00 | 2 | MED RECORD COPY PER PAGE | |
| S9988 | | $459.00 | 2 | SERV PART OF PHASE I TRIAL | |
| | | | | Total | $77,365.90 |

*FIG. 6b*

SIU# 04-110005

DIAGNOSIS CODE DEFINITIONS

PATIENT: TEST TEST
CLAIM NUMBER: 0000
DATE OF BIRTH: 12/31/1999
DATE OF INJURY: 05/28/2007

| Code | Description |
|---|---|
| 722.0 | DISPLACEMENT OF CERVICAL INTERVERTEBRAL DISC WITHOUT MYELOPATHY |
| 724.3 | SCIATICA |
| 724.4 | THORACIC OR LUMBOSACRAL NEURITIS OR RADICULITIS UNSPECIFIED |
| 953.0 | INJURY TO CERVICAL NERVE ROOT |

2/11/2011

SIU# 04-110005

FLOW TREATMENT BY PROVIDER

SIU Review, inc

PATIENT: TEST Testing JR
CLAIM NUMBER: 0000
DATE OF BIRTH: 12/31/1999
DATE OF INJURY: 05/28/2007

| Provider Code | DOS | Mod | ICD-9 CM | Charge | Prior MDA | | | Additional Comments |
|---|---|---|---|---|---|---|---|---|
| PROVIDER 1 | | | | | | | | |
| 62290 | 03/19/2009 | | | $1,250.00 | Yes | No | | |
| 62290 | 03/19/2009 | | | $2,500.00 | Yes | No | | |
| 72295 | 03/19/2009 | | | $600.00 | Yes | No | | |
| 72295 | 03/19/2009 | | | $600.00 | Yes | No | | |
| 99070 | 03/19/2009 | | | $498.00 | Yes | No | | |
| 99144 | 03/19/2009 | | | $500.00 | Yes | No | | |
| 99243 | 03/19/2009 | | | $375.00 | Yes | No | | |
| A4461 | 03/19/2009 | | | $200.00 | Yes | No | | |
| J0690 | 03/19/2009 | | | $2.85 | Yes | No | | |
| J1885 | 03/19/2009 | | | $11.50 | Yes | No | | |
| J2175 | 03/19/2009 | | | $1.85 | Yes | No | | |
| J7050 | 03/19/2009 | | | $10.00 | Yes | No | | |
| 62291 | 04/30/2009 | | | $1,800.00 | Yes | No | | |
| 62291 | 04/30/2009 | | | $3,600.00 | Yes | No | | |
| 72285 | 04/30/2009 | | | $600.00 | Yes | No | | |
| 72285 | 04/30/2009 | | | $600.00 | Yes | No | | |
| 99070 | 04/30/2009 | | | $498.00 | Yes | No | | |
| 99144 | 04/30/2009 | | | $500.00 | Yes | No | | |
| E0942 | 04/30/2009 | | | $200.00 | Yes | No | | |
| J0690 | 04/30/2009 | | | $2.85 | Yes | No | | |
| J2175 | 04/30/2009 | | | $1.85 | Yes | No | | |
| J7050 | 04/30/2009 | | | $10.00 | Yes | No | | |
| PROVIDER 2 | | | | | | | | |
| 99244 | 02/12/2009 | | | $1,000.00 | Yes | No | | |
| 00000 | 03/19/2009 | | | $200.00 | Yes | No | | |
| 62287 | 03/19/2009 | | | $20,000.00 | Yes | No | | |
| 99070 | 03/19/2009 | | | $4,000.00 | Yes | No | | |
| S9962 | 03/19/2009 | | | $200.00 | Yes | No | | |
| S9988 | 03/19/2009 | | | $234.00 | Yes | No | | |
| 72100 | 04/17/2009 | | | $150.00 | Yes | No | | |
| 99024 | 04/17/2009 | | | $0.00 | Yes | No | | |
| 00000 | 04/30/2009 | | | $200.00 | Yes | No | | |
| 64999 | 04/30/2009 | | | $20,000.00 | Yes | No | | |
| 99070 | 04/30/2009 | | | $4,000.00 | Yes | No | | |
| S9962 | 04/30/2009 | | | $200.00 | Yes | No | | |
| S9988 | 04/30/2009 | | | $225.00 | Yes | No | | |
| 72070 | 05/26/2009 | | | $200.00 | Yes | No | | |
| 99024 | 05/26/2009 | | | $0.00 | Yes | No | | |
| 99024 | 06/30/2009 | | | $0.00 | Yes | No | | |
| 99214 | 07/28/2009 | | | $400.00 | Yes | No | | |
| 99024 | 09/30/2009 | | | $0.00 | Yes | No | | |
| 20552 | 11/19/2009 | | | $350.00 | Yes | No | | |
| 99213 | 11/19/2009 | 25 | | $300.00 | Yes | No | | |
| J2001 | 11/19/2009 | | | $25.00 | Yes | No | | |
| J3301 | 11/19/2009 | | | $16.00 | Yes | No | | |
| PROVIDER 3 | | | | | | | | |
| 72141 | 12/01/2008 | | | $1,850.00 | Yes | No | | |
| 72148 | 12/01/2008 | | | $1,850.00 | Yes | No | | |
| PROVIDER 4 | | | | | | | | |
| 72040 | 01/15/2009 | | [722.0],953.0 | $155.00 | Yes | No | | |
| 72110 | 01/15/2009 | | 724.3,724.4 | $250.00 | Yes | No | | |
| 72170 | 01/15/2009 | | 724.3,724.4 | $100.00 | Yes | No | | |
| PROVIDER 5 | | | | | | | | |
| 97010 | 10/20/2008 | | | $45.00 | Yes | No | | |
| 97010 | 10/21/2008 | | | $45.00 | Yes | No | | |
| 97010 | 10/22/2008 | | | $45.00 | Yes | No | | |
| 97014 | 10/20/2008 | | | $30.00 | Yes | No | | |
| 97014 | 10/21/2008 | | | $30.00 | Yes | No | | |
| 97014 | 10/22/2008 | | | $30.00 | Yes | No | | |

SIU# 04-110005

FLOW TREATMENT BY PROVIDER

PATIENT: TEST Testing JR
CLAIM NUMBER: 0000
DATE OF BIRTH: 12/31/1999
DATE OF INJURY: 05/28/2007

| Provider Code | DOS | Mod | ICD-9 CM | Charge | Prior MDA | | Additional Comments |
|---|---|---|---|---|---|---|---|
| PROVIDER 5 | | | | | | | |
| 97035 | 10/20/2008 | | | $30.00 | Yes | No | |
| 97035 | 10/21/2008 | | | $30.00 | Yes | No | |
| 97035 | 10/22/2008 | | | $30.00 | Yes | No | |
| 97110 | 10/20/2008 | | | $60.00 | Yes | No | |
| 97112 | 10/21/2008 | | | $60.00 | Yes | No | |
| 97112 | 10/22/2008 | | | $60.00 | Yes | No | |
| 97140 | 10/20/2008 | | | $55.00 | Yes | No | |
| 97140 | 10/21/2008 | | | $55.00 | Yes | No | |
| 97140 | 10/22/2008 | | | $55.00 | Yes | No | |
| 99202 | 10/20/2008 | | | $135.00 | Yes | No | |
| 99211 | 10/21/2008 | | | $55.00 | Yes | No | |
| 99211 | 10/22/2008 | | | $55.00 | Yes | No | |
| 99242 | 10/21/2008 | | | $350.00 | Yes | No | |
| 97010 | 10/28/2008 | | | $45.00 | Yes | No | |
| 97010 | 10/29/2008 | | | $45.00 | Yes | No | |
| 97010 | 10/31/2008 | | | $45.00 | Yes | No | |
| 97014 | 10/28/2008 | | | $30.00 | Yes | No | |
| 97014 | 10/29/2008 | | | $30.00 | Yes | No | |
| 97014 | 10/31/2008 | | | $30.00 | Yes | No | |
| 97035 | 10/29/2008 | | | $30.00 | Yes | No | |
| 97035 | 10/31/2008 | | | $30.00 | Yes | No | |
| 97039 | 10/28/2008 | | | $30.00 | Yes | No | |
| 97110 | 10/28/2008 | | | $60.00 | Yes | No | |
| 97110 | 10/29/2008 | | | $60.00 | Yes | No | |
| 97110 | 10/31/2008 | | | $60.00 | Yes | No | |
| 97112 | 10/28/2008 | | | $60.00 | Yes | No | |
| 97112 | 10/29/2008 | | | $60.00 | Yes | No | |
| 97112 | 10/31/2008 | | | $60.00 | Yes | No | |
| 97140 | 10/28/2008 | | | $55.00 | Yes | No | |
| 97140 | 10/29/2008 | | | $55.00 | Yes | No | |
| 97140 | 10/31/2008 | | | $55.00 | Yes | No | |
| 99211 | 10/28/2008 | | | $55.00 | Yes | No | |
| 99211 | 10/29/2008 | | | $55.00 | Yes | No | |
| 99211 | 10/31/2008 | | | $55.00 | Yes | No | |
| 97010 | 11/03/2008 | | | $45.00 | Yes | No | |
| 97010 | 11/05/2008 | | | $45.00 | Yes | No | |
| 97014 | 11/03/2008 | | | $30.00 | Yes | No | |
| 97014 | 11/05/2008 | | | $30.00 | Yes | No | |
| 97035 | 11/03/2008 | | | $30.00 | Yes | No | |
| 97035 | 11/05/2008 | | | $30.00 | Yes | No | |
| 97110 | 11/03/2008 | | | $60.00 | Yes | No | |
| 97110 | 11/05/2008 | | | $60.00 | Yes | No | |
| 97112 | 11/03/2008 | | | $60.00 | Yes | No | |
| 97112 | 11/05/2008 | | | $60.00 | Yes | No | |
| 97140 | 11/03/2008 | | | $55.00 | Yes | No | |
| 97140 | 11/05/2008 | | | $55.00 | Yes | No | |
| 99211 | 11/03/2008 | | | $55.00 | Yes | No | |
| 99211 | 11/05/2008 | | | $55.00 | Yes | No | |
| 97010 | 11/10/2008 | | | $45.00 | Yes | No | |
| 97010 | 11/12/2008 | | | $45.00 | Yes | No | |
| 97010 | 11/14/2008 | | | $45.00 | Yes | No | |
| 97014 | 11/10/2008 | | | $30.00 | Yes | No | |
| 97014 | 11/12/2008 | | | $30.00 | Yes | No | |
| 97014 | 11/14/2008 | | | $30.00 | Yes | No | |
| 97035 | 11/10/2008 | | | $30.00 | Yes | No | |
| 97035 | 11/12/2008 | | | $30.00 | Yes | No | |
| 97035 | 11/14/2008 | | | $30.00 | Yes | No | |
| 97110 | 11/10/2008 | | | $60.00 | Yes | No | |
| 97110 | 11/12/2008 | | | $60.00 | Yes | No | |
| 97110 | 11/14/2008 | | | $60.00 | Yes | No | |
| 97112 | 11/10/2008 | | | $60.00 | Yes | No | |
| 97112 | 11/12/2008 | | | $60.00 | Yes | No | |
| 97112 | 11/14/2008 | | | $60.00 | Yes | No | |

SIU# 04-110005

FLOW TREATMENT BY PROVIDER

SIU Review, inc

PATIENT: TEST Testing JR
CLAIM NUMBER: 0000
DATE OF BIRTH: 12/31/1999
DATE OF INJURY: 05/28/2007

| Provider Code | DOS | Mod | ICD-9 CM | Charge | Prior MDA | | Additional Comments |
|---|---|---|---|---|---|---|---|
| PROVIDER 5 | | | | | | | |
| 97140 | 11/10/2008 | | | $55.00 | Yes | No | |
| 97140 | 11/12/2008 | | | $55.00 | Yes | No | |
| 97140 | 11/14/2008 | | | $55.00 | Yes | No | |
| 99211 | 11/10/2008 | | | $55.00 | Yes | No | |
| 99211 | 11/12/2008 | | | $55.00 | Yes | No | |
| 99211 | 11/14/2008 | | | $55.00 | Yes | No | |
| 97010 | 11/17/2008 | | | $45.00 | Yes | No | |
| 97010 | 11/20/2008 | | | $45.00 | Yes | No | |
| 97010 | 11/21/2008 | | | $45.00 | Yes | No | |
| 97014 | 11/17/2008 | | | $30.00 | Yes | No | |
| 97014 | 11/20/2008 | | | $30.00 | Yes | No | |
| 97014 | 11/21/2008 | | | $30.00 | Yes | No | |
| 97035 | 11/17/2008 | | | $30.00 | Yes | No | |
| 97035 | 11/20/2008 | | | $30.00 | Yes | No | |
| 97035 | 11/21/2008 | | | $30.00 | Yes | No | |
| 97110 | 11/17/2008 | | | $60.00 | Yes | No | |
| 97110 | 11/20/2008 | | | $60.00 | Yes | No | |
| 97110 | 11/21/2008 | | | $60.00 | Yes | No | |
| 97112 | 11/17/2008 | | | $60.00 | Yes | No | |
| 97112 | 11/20/2008 | | | $60.00 | Yes | No | |
| 97112 | 11/21/2008 | | | $60.00 | Yes | No | |
| 97140 | 11/17/2008 | | | $55.00 | Yes | No | |
| 97140 | 11/20/2008 | | | $55.00 | Yes | No | |
| 97140 | 11/21/2008 | | | $55.00 | Yes | No | |
| 99211 | 11/17/2008 | | | $55.00 | Yes | No | |
| 99211 | 11/20/2008 | | | $55.00 | Yes | No | |
| 99211 | 11/21/2008 | | | $55.00 | Yes | No | |
| 97014 | 11/24/2008 | | | $30.00 | Yes | No | |
| 97110 | 11/24/2008 | | | $60.00 | Yes | No | |
| 97112 | 11/24/2008 | | | $60.00 | Yes | No | |
| 97140 | 11/24/2008 | | | $55.00 | Yes | No | |
| 99212 | 11/24/2008 | | | $80.00 | Yes | No | |
| 97010 | 12/01/2008 | | | $45.00 | Yes | No | |
| 97010 | 12/03/2008 | | | $45.00 | Yes | No | |
| 97010 | 12/05/2008 | | | $45.00 | Yes | No | |
| 97014 | 12/01/2008 | | | $30.00 | Yes | No | |
| 97014 | 12/03/2008 | | | $30.00 | Yes | No | |
| 97014 | 12/05/2008 | | | $30.00 | Yes | No | |
| 97035 | 12/01/2008 | | | $30.00 | Yes | No | |
| 97035 | 12/03/2008 | | | $30.00 | Yes | No | |
| 97035 | 12/05/2008 | | | $30.00 | Yes | No | |
| 97110 | 12/01/2008 | | | $60.00 | Yes | No | |
| 97110 | 12/03/2008 | | | $60.00 | Yes | No | |
| 97112 | 12/01/2008 | | | $60.00 | Yes | No | |
| 97112 | 12/03/2008 | | | $60.00 | Yes | No | |
| 97112 | 12/05/2008 | | | $60.00 | Yes | No | |
| 97140 | 12/01/2008 | | | $55.00 | Yes | No | |
| 97140 | 12/03/2008 | | | $55.00 | Yes | No | |
| 97140 | 12/05/2008 | | | $55.00 | Yes | No | |
| 99211 | 12/01/2008 | | | $55.00 | Yes | No | |
| 99211 | 12/03/2008 | | | $55.00 | Yes | No | |
| 99211 | 12/05/2008 | | | $55.00 | Yes | No | |
| 97010 | 12/10/2008 | | | $45.00 | Yes | No | |
| 97012 | 12/08/2008 | | | $40.00 | Yes | No | |
| 97014 | 12/10/2008 | | | $30.00 | Yes | No | |
| 97035 | 12/10/2008 | | | $30.00 | Yes | No | |
| 97110 | 12/08/2008 | | | $60.00 | Yes | No | |
| 97112 | 12/08/2008 | | | $60.00 | Yes | No | |
| 97112 | 12/08/2008 | | | $60.00 | Yes | No | |
| 97140 | 12/08/2008 | | | $55.00 | Yes | No | |
| 97140 | 12/10/2008 | | | $55.00 | Yes | No | |
| 99211 | 12/08/2008 | | | $55.00 | Yes | No | |
| 99212 | 12/10/2008 | | | $80.00 | Yes | No | |
| 97010 | 01/02/2009 | | | $45.00 | Yes | No | |
| 97014 | 01/02/2009 | | | $30.00 | Yes | No | |

SIU# 04-110005

FLOW TREATMENT BY PROVIDER

PATIENT: TEST Testing JR
CLAIM NUMBER: 0000
DATE OF BIRTH: 12/31/1999
DATE OF INJURY: 05/28/2007

| Provider Code | DOS | Mod | ICD-9 CM | Charge | Prior MDA | Additional Comments |
|---|---|---|---|---|---|---|
| PROVIDER 5 | | | | | | |
| 97035 | 01/02/2009 | | | $30.00 | Yes ☐ No ☐ | |
| 97110 | 01/02/2009 | | | $60.00 | Yes ☐ No ☐ | |
| 97112 | 01/02/2009 | | | $60.00 | Yes ☐ No ☐ | |
| 97140 | 01/02/2009 | | | $55.00 | Yes ☐ No ☐ | |
| 99212 | 01/02/2009 | | | $80.00 | Yes ☐ No ☐ | |

Total Charges $77,365.90

SIU# 04-110005

PROVIDER BILLING SUMMARY

SIU Review, inc

PATIENT: TEST TEST
CLAIM NUMBER: 0000
DATE OF BIRTH: 12/31/1999
DATE OF INJURY: 05/28/2007

| Provider | Tax ID | Dates of Service From | To | Charge | Bills |
|---|---|---|---|---|---|
| PROVIDER 1 | 11111111 | 03/19/2009 | 04/30/2009 | $14,361.90 | 1 |
| PROVIDER 2 | 22222222 | 02/12/2009 | 11/19/2009 | $51,699.00 | 1 |
| PROVIDER 3 | 33333333 | 12/01/2008 | 12/01/2008 | $3,700.00 | 1 |
| PROVIDER 4 | 44444444 | 01/15/2009 | 01/15/2009 | $505.00 | 1 |
| PROVIDER 5 | 55555555 | 10/20/2008 | 01/02/2009 | $7,100.00 | 3 |
| | | | Total Charges | $77,365.90 | |

2/11/2011

SIU# 04-110005  PROVIDER BILLING BY CODE SECTION 
PATIENT: TEST TEST
CLAIM NUMBER: 0000
DATE OF BIRTH: 12/31/1999
DATE OF INJURY: 05/28/2007
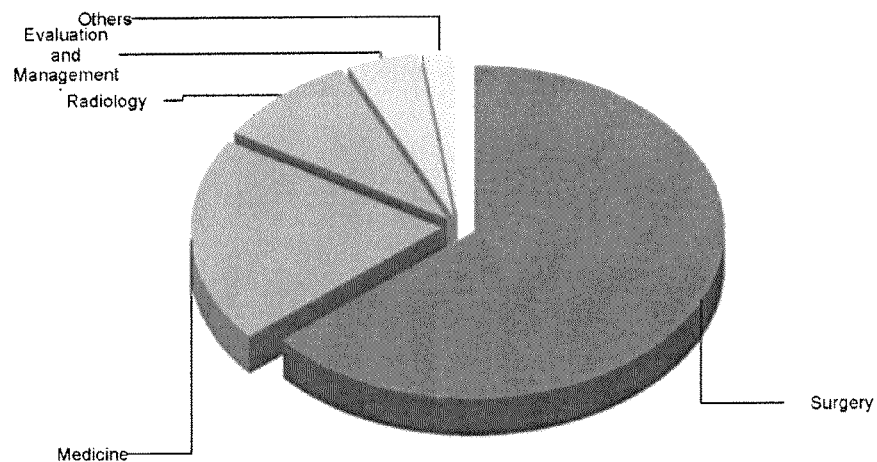
| | | | |
|---|---|---:|---:|
| ■ | Surgery | $49,500.00 | 64.0% |
| ▦ | Medicine | $15,436.00 | 20.0% |
| ▨ | Radiology | $6,955.00 | 9.0% |
| | Evaluation and Management | $3,735.00 | 4.8% |
| | Others | $1,739.90 | 2.2% |
| | Total: | $77,365.90 | 100.0% |
*FIG. 11a*

SIU# 04-110005

PROVIDER BILLING BY CODE SECTION

SIU Review, inc

PATIENT: TEST TEST
CLAIM NUMBER: 0000
DATE OF BIRTH: 12/31/1999
DATE OF INJURY: 05/28/2007

| CPT™ Section<br>Provider | Tax ID | Dates of Service | | Charge | Bills |
|---|---|---|---|---|---|
| | | From | To | | |
| *Not Assigned* | | | | *$400.00* | |
| PROVIDER 2 | 22222222 | 03/19/2009 | 04/30/2009 | $400.00 | 1 |
| *Evaluation and Management* | | | | *$3,735.00* | |
| PROVIDER 1 | 11111111 | 03/19/2009 | 03/19/2009 | $375.00 | 1 |
| PROVIDER 2 | 22222222 | 02/12/2009 | 11/19/2009 | $1,700.00 | 1 |
| PROVIDER 5 | 55555555 | 10/20/2008 | 01/02/2009 | $1,660.00 | 3 |
| *Surgery* | | | | *$49,500.00* | |
| PROVIDER 1 | 11111111 | 03/19/2009 | 04/30/2009 | $9,150.00 | 1 |
| PROVIDER 2 | 22222222 | 03/19/2009 | 11/19/2009 | $40,350.00 | 1 |
| *Radiology* | | | | *$6,955.00* | |
| PROVIDER 1 | 11111111 | 03/19/2009 | 04/30/2009 | $2,400.00 | 1 |
| PROVIDER 2 | 22222222 | 04/17/2009 | 05/26/2009 | $350.00 | 1 |
| PROVIDER 3 | 33333333 | 12/01/2008 | 12/01/2008 | $3,700.00 | 1 |
| PROVIDER 4 | 44444444 | 01/15/2009 | 01/15/2009 | $505.00 | 1 |
| *Medicine* | | | | *$15,436.00* | |
| PROVIDER 1 | 11111111 | 03/19/2009 | 04/30/2009 | $1,996.00 | 1 |
| PROVIDER 2 | 22222222 | 03/19/2009 | 09/30/2009 | $8,000.00 | 1 |
| PROVIDER 5 | 55555555 | 10/20/2008 | 01/02/2009 | $5,440.00 | 2 |
| *Medical and Surgical Supplies* | | | | *$200.00* | |
| PROVIDER 1 | 11111111 | 03/19/2009 | 03/19/2009 | $200.00 | 1 |
| *Durable Medical Equipment* | | | | *$200.00* | |
| PROVIDER 1 | 11111111 | 04/30/2009 | 04/30/2009 | $200.00 | 1 |
| *Drugs* | | | | *$80.90* | |
| PROVIDER 1 | 11111111 | 03/19/2009 | 04/30/2009 | $40.90 | 1 |
| PROVIDER 2 | 22222222 | 11/19/2009 | 11/19/2009 | $40.00 | 1 |
| *Temporary National Codes* | | | | *$859.00* | |
| PROVIDER 2 | 22222222 | 03/19/2009 | 04/30/2009 | $859.00 | 1 |
| | | | Total Charges | $77,365.90 | |

SIU# 04-110005

CCI EDITS

SIU Review, inc

PATIENT: TEST TEST
CLAIM NUMBER: 0000
DATE OF BIRTH: 12/31/1999
DATE OF INJURY: 05/28/2007

PROVIDER 1
100 Orange, Suite 100 Miami FL 32523

Tax ID #
Charged $4,125.00

| Code | Modifier | Charge | Dates of Service From | To |
|---|---|---|---|---|
| 62290 | | $3,750.00 | 03/19/2009 | 03/19/2009 |

CPT™ code 62290 activities are included in the CPT™ code 62287.

| 99243 | | $375.00 | 03/19/2009 | 03/19/2009 |

CPT™ code 99243 activities are included in the CPT™ code 99144.

PROVIDER 2
200 Street Miami FL 32523

Tax ID #
Charged $20,425.00

| Code | Modifier | Charge | Dates of Service From | To |
|---|---|---|---|---|
| 00000 | | $400.00 | 03/19/2009 | 04/30/2009 |

Code 00000 is unknown, invalid, or may be represent by Revenue code(s).

| 64999 | | $20,000.00 | 04/30/2009 | 04/30/2009 |

CPT™ Code 64999 is an Unlisted service or procedure. A special report describing nature, extent, need for the procedure, and the time, effort, equipment necessary to provide the service is required.

| J2001 | | $25.00 | 11/19/2009 | 11/19/2009 |

CPT™ code J2001 activities are included in the CPT™ code 20552.

PROVIDER 5
500 River, Suite 200 Miami FL 32523

Tax ID #
Charged $85.00

| Code | Modifier | Charge | Dates of Service From | To |
|---|---|---|---|---|
| 97039 | | $30.00 | 10/28/2008 | 10/28/2008 |

CPT™ Code 97039 is an Unlisted service or procedure. A special report describing nature, extent, need for the procedure, and the time, effort, equipment necessary to provide the service is required.

| 97140 | | $55.00 | 12/08/2008 | 12/08/2008 |

CPT™ code 97012 cannot reasonably be performed on the same date of service as CPT™ code 97140. Adequacy of documentation supporting the use of this code should be assessed Total Non-reimbursable Charges : $24,635.00

SIU# 04-110005

RED FLAGS

SIU Review, inc

PATIENT: TEST TEST
CLAIM NUMBER: 0000
DATE OF BIRTH: 12/31/1999
DATE OF INJURY: 05/28/2007

PROVIDER 1  Tax ID #
100 Orange, Suite 100 Miami FL 32523

Description

Consult CPT™ Code 99243 is utilized without providing the name of the referring physician.

CPT™ code 62290 activities are included in the CPT™ code 62287.

CPT™ code 99243 activities are included in the CPT™ code 99144.

PROVIDER 2  Tax ID #
200 Street Miami FL 32523

Description

Code 00000 is unknown, invalid, or may be represent by Revenue code(s).

Consult CPT™ Code 99244 is utilized without providing the name of the referring physician.

CPT™ code 62290 activities are included in the CPT™ code 62287.

CPT™ Code 64999 is an Unlisted service or procedure. A special report describing nature, extent, need for the procedure, and the time, effort, equipment necessary to provide the service is required.

CPT™ code J2001 activities are included in the CPT™ code 20552.

Place of Service code 17 is unknown.

PROVIDER 5  Tax ID #
500 River, Suite 200 Miami FL 32523

Description

CPT™ code 97012 cannot reasonably be performed on the same date of service as CPT™ code 97140. Adequacy of documentation supporting the use of this code should be assessed.

CPT™ Code 97039 is an Unlisted service or procedure. A special report describing nature, extent, need for the procedure, and the time, effort, equipment necessary to provide the service is required.

SIU# 04-110005

PROVIDER BILLING

PATIENT: TEST TEST
CLAIM NUMBER: CCCC
DATE OF BIRTH: 12/31/1999
DATE OF INJURY: 05/28/2007

| Code | Modifier | Description | | | Charge | Count |
|---|---|---|---|---|---|---|
| PROVIDER 1 | | | Tax ID: 11111111 | | $14,361.90 | |
| 100 Orange, Suite 100 Miami FL 32523 | | | DOS: 03/19/2009 | 04/30/2009 | | |
| 62290 | | NJX DISKOGRAPY EA LVL LMBR | | | $3,750.00 | 2 |
| 62291 | | NJX DISKOGRAPY EA LVL CRV/THRC | | | $5,400.00 | 2 |
| 72285 | | DISKOGRAPY CRV/THRC RS&I | | | $1,200.00 | 2 |
| 72295 | | DISKOGRAPY LMBR RS&I | | | $1,200.00 | 2 |
| 99070 | | SUPPLIES&MATERIALS PRV BY PHYS >&ABOVE | | | $996.00 | 2 |
| 99144 | | M-SEDAJ BY SM PHYS PERFRMG SVC 5+ YR | | | $1,000.00 | 2 |
| 99243 | | OFFICE CONSLTJ 40 MIN | | | $375.00 | 1 |
| A4461 | | SURGICL DRESS HOLD NON-REUSE | | | $200.00 | 1 |
| E0942 | | CERVICAL HEAD HARNESS/HALTER | | | $200.00 | 1 |
| J0690 | | CEFAZOLIN SODIUM INJECTION | | | $5.70 | 2 |
| J1885 | | KETOROLAC TROMETHAMINE INJ | | | $11.50 | 1 |
| J2175 | | MEPERIDINE HYDROCHL /100 MG | | | $3.70 | 2 |
| J7050 | | NORMAL SALINE SOLUTION INFUS | | | $20.00 | 2 |
| PROVIDER 2 | | | Tax ID: 22222222 | | $51,699.00 | |
| 200 Street Miami FL 32523 | | | DOS: 02/12/2009 | 11/19/2009 | | |
| 00000 | | DESCRIPTION NOT FOUND | | | $400.00 | 2 |
| 20552 | | INJECTION SINGLE/MLT TRIGGER POINT 1/2 MUSCLES | | | $350.00 | 1 |
| 62287 | | DCMPRN PERQ NUCLEUS PULPOSUS 1/> LEVELS LUMBAR | | | $20,000.00 | 1 |
| 64999 | | UNLIS PX NRVS SYS | | | $20,000.00 | 1 |
| 72070 | | RADEX SPI THRC 2 VIEWS | | | $200.00 | 1 |
| 72100 | | RADEX SPI LUMBOSAC 2/3 VIEWS | | | $150.00 | 1 |
| 99024 | | PO F-UP VST RELATED TO ORIGINAL PX | | | $0.00 | 4 |
| 99070 | | SUPPLIES&MATERIALS PRV BY PHYS >&ABOVE | | | $8,000.00 | 2 |
| 99213 | 25 | OFFICE OUTPT EST 15 MIN | | | $300.00 | 1 |
| 99214 | | OFFICE OUTPT EST 25 MIN | | | $400.00 | 1 |
| 99244 | | OFFICE CONSLTJ 60 MIN | | | $1,000.00 | 1 |
| J2001 | | LIDOCAINE INJECTION | | | $25.00 | 1 |
| J3301 | | TRIAMCINOLONE ACET INJ NOS | | | $15.00 | 1 |
| S9982 | | MED RECORD COPY PER PAGE | | | $400.00 | 2 |
| S9988 | | SERV PART OF PHASE I TRIAL | | | $459.00 | 2 |
| PROVIDER 3 | | | Tax ID: 33333333 | | $3,700.00 | |
| 300 Main Avenue Miami FL 32523 | | | DOS: 12/01/2008 | 12/01/2008 | | |
| 72141 | | MRI SPI CANAL&CNTS CRV C-MATRL | | | $1,850.00 | 1 |
| 72148 | | MRI SPI CANAL&CNTS LMBR C-MATRL | | | $1,850.00 | 1 |
| PROVIDER 4 | | | Tax ID: 44444444 | | $505.00 | |
| 400 Tamiami Road Miami FL 32523 | | | DOS: 01/15/2009 | 01/15/2009 | | |
| 72040 | | RADEX SPI CRV 2/3 VIEWS | | | $155.00 | 1 |
| 72110 | | RADEX SPI LUMBOSAC MINIMUM 4 VIEWS | | | $250.00 | 1 |
| 72170 | | RADEX PELVIS 1/2 VIEWS | | | $100.00 | 1 |

SIU# 04-110005

PROVIDER BILLING

SIU Review, inc

PATIENT: TEST TEST
CLAIM NUMBER: 0000
DATE OF BIRTH: 12/31/1999
DATE OF INJURY: 05/28/2007

| Code | Modifier | Description | | | | Charge | Count |
|---|---|---|---|---|---|---|---|
| PROVIDER 5 | | | Tax ID: | 55555555 | | $7,100.00 | |
| 500 River, Suite 200 Miami FL 32523 | | | DOS: | 10/20/2008 | 01/02/2009 | | |
| 97010 | | APPL MODALITY 1+ AREAS HOT/COLD PACKS | | | | $855.00 | 19 |
| 97012 | | APPL MODALITY 1+ AREAS TRCJ MCHNL | | | | $40.00 | 1 |
| 97014 | | APPL MODALITY 1+ AREAS ELEC STIMJ UNATTN | | | | $600.00 | 20 |
| 97035 | | APPL MODALITY 1+ AREAS US EA 15 MIN | | | | $540.00 | 18 |
| 97039 | | UNLIS MODALITY SPEC TYP&TM IF CONSTANT ATTN | | | | $30.00 | 1 |
| 97110 | | THER PX 1+ AREAS EA 15 MIN THER XERSS | | | | $1,020.00 | 17 |
| 97112 | | THER PX 1+ AREAS EA 15 MIN NEUROMUSC REEDUCAJ | | | | $1,200.00 | 20 |
| 97140 | | MNL THER TQS 1+ REGIONS EA 15 MIN | | | | $1,155.00 | 21 |
| 99202 | | OFFICE OUTPT NEW 20 MINUTES | | | | $135.00 | 1 |
| 99211 | | OFFICE O/P EST 5 MIN | | | | $935.00 | 17 |
| 99212 | | OFFICE OUTPT EST 10 MIN | | | | $240.00 | 3 |
| 99242 | | OFFICE CONSLTJ 30 MIN | | | | $360.00 | 1 |
| | | | | | Total Charges | $77,365.90 | |

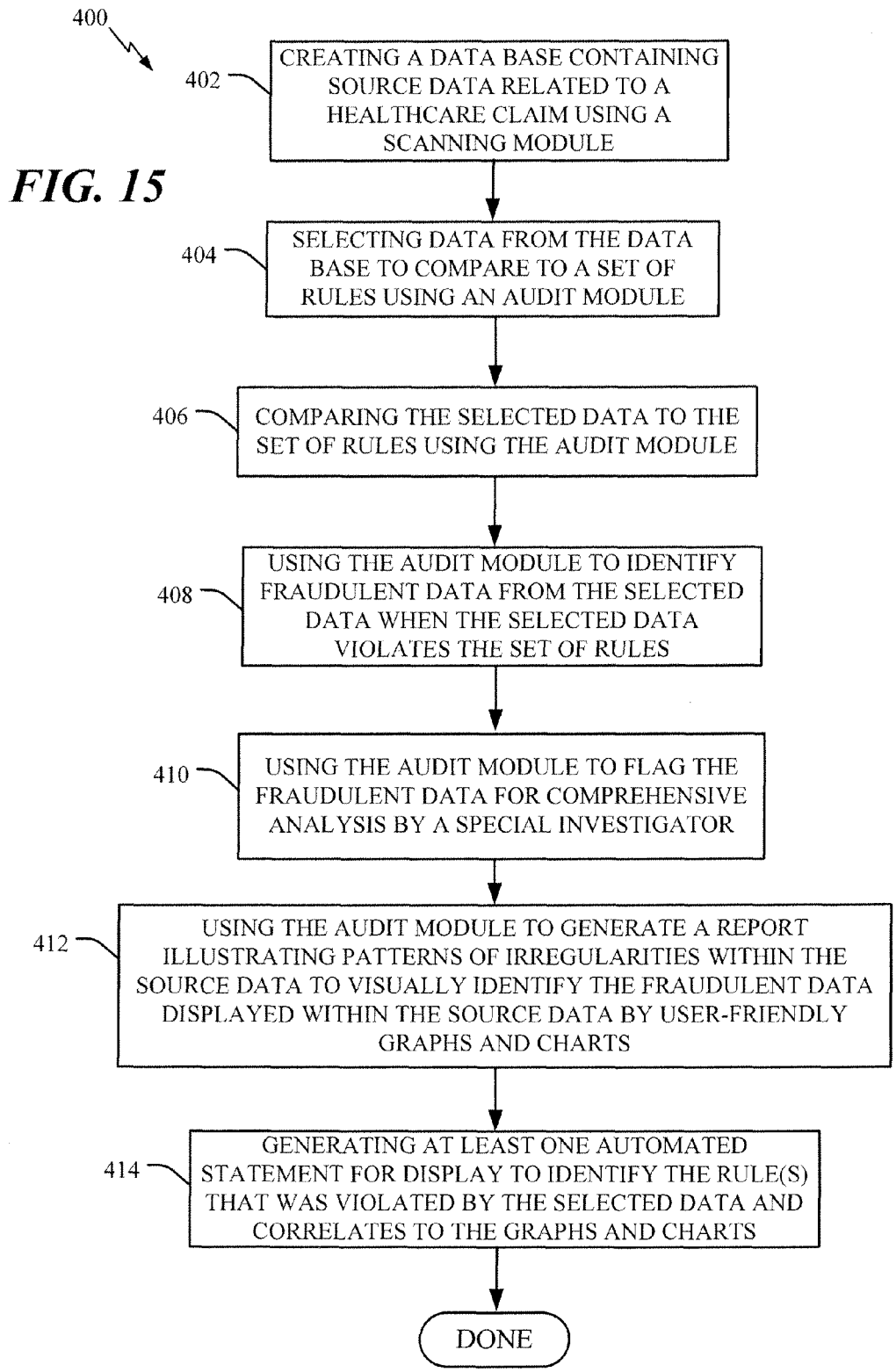

SYSTEM AND METHOD FOR DETECTING HEALTHCARE INSURANCE FRAUD

I. CROSS REFERENCE TO RELATED APPLICATIONS

This application is a continuation of U.S. patent application Ser. No. 11/938,582 filed Nov. 12, 2007, entitled "System and Method for Detecting Healthcare Insurance Fraud" and also claims the benefit of U.S. provisional patent application Ser. 60/865,400 filed Nov. 10, 2006.

II. FIELD OF THE INVENTION

The present invention relates generally to the healthcare industry, and more specifically to analyzing data submitted by healthcare providers and detecting fraudulent activity.

III. BACKGROUND

Though industry experts say that the cost of fraud in the healthcare industry is somewhere between $67-$224 billion—in one year alone which is passed on to consumers in the form of higher premiums. Many healthcare insurers are reluctant to hire Special Investigative Units (SIU's) to identify and fight fraud because they are perceived as costly and a risk that could potentially expose the insurer to bad-faith lawsuits. SIU agents are usually made up of a team of highly trained investigators, with law enforcement background and have specialized training and experience in the investigation of suspect insurance claims submitted by healthcare providers for reimbursement. Traditional claims investigations take many hours to complete and experienced investigators generally command high salaries. Vast amounts of claim forms and medical documentation has to be sorted, studied, and compared to industry guidelines, annual coding updates, tri-annual CCI updates, national/international rules and regulations, as well as applicable state statutes, regulations, rules and program requirements for the investigator to arrive at an opinion as to whether fraud has been detected.

Accordingly, there is a need in the art for a method and system that enables an investigator to analyze data and to detect fraud much faster, saving time and money for insurance companies, SIU agents, Federal agencies (DHHS), federal government, adjusters, claims management and state departments.

There is also a need in the art for a method that generates output from the data analyzation that is flexible so that it can be provided to an expert witness for evaluation or sent to attorney or insurance carrier without unnecessary, privileged or confidential information.

There is a need in the art for a method and system that reduces labor-intensive responsibilities and lowers overall expenses of analyzing the data but maintains quality assurance capabilities.

There is a need in the art for a method and system that has the ability to analyze the data across multiple healthcare providers, unique physician/practitioner identification numbers (UPIN#s), national provider identifier numbers (NPI#s), tax identification numbers (TIN#s), locations, Durable Medical Equipment (DME) suppliers, patient/claimants, occurrences, procedures, diseases/conditions and provider charges.

There is a need in the art for a method and system that has the ability to analyze patterns within the data and to generate user-friendly reports and color-coded graphs/charts.

There is a need in the art for a method and system that allows a user to define rules that generate an alert or flag contemporaneously with the analyzation of the data when the data being analyzed meets the user-defined set of rules.

There is a need in the art for a method and system that is adaptable to a user's specialized areas of interest for specific investigative projects.

There is a need in the art for a method and system with a user reference library on instructions on the proper use of medical equipment and devices, clinic inspection techniques, manufacturer specs of diagnostic equipment, required OIG Physician Compliance Program information, appropriate medical record keeping requirements, definitions of HCPCS/CPT® and ICD-9/ICD-10 codes, which are relevant to the data analyzation and fraud detection.

There is also a need in the art for a method and system that is flexible to adapt to meet a healthcare provider, insurers, legal counsel, SIU and Federal Government needs in terms of generating output, access, flags, patterning and search criteria.

It is, therefore, to the effective resolution of the aforementioned problems and shortcomings of the prior art that the present invention is directed.

However, in view of the prior art at the time the present invention was made, it was not obvious to those of ordinary skill in the pertinent art how the identified needs could be fulfilled.

IV. SUMMARY

The following presents a simplified summary of one or more embodiments in order to provide a basic understanding of some aspects of such embodiments. This summary is not an extensive overview of the one or more embodiments, and is intended to neither identify key or critical elements of the embodiments nor delineate the scope of such embodiments. Its sole purpose is to present some concepts of the described embodiments in a simplified form as a prelude to the more detailed description that is presented later.

A system and method for detecting healthcare billing and insurance fraud is disclosed. The method includes creating a database containing source data related to at least one healthcare claim submitted for reimbursement, selecting data from the database to compare to a set of rules using an audit module, and comparing the selected data to the set of rules using the audit module. The method also includes using the audit module to automatically identify suspected fraudulent data when the selected data violates at least one rule of the set of rules and using the audit module to flag the fraudulent data. In addition, the method includes using the audit module to generate a report illustrating patterns of irregularities within the source data to visually identify the fraudulent data displayed within the source data by user-friendly graphs and charts, and generating at least one automated statement for display to identify at least one rule of the set of rules that was violated by the selected data using a documentation module.

In another particular embodiment, a system of detecting and identifying abuse, over-utilization and fraud arising from a healthcare bill/claim submitted for reimbursement is disclosed. The system includes a storage means for storing a database containing source data related to a healthcare claim. A memory means is used for storing a set of user-defined rules for detecting and identifying fraud. The set of rules includes, but is not limited to, specific requirements in determining if the proper patient history, examination and medical decision making process of a patient was documented/performed prior to ordering diagnostic test; a quantity rule to determine if diagnostic tests ordered correlate to a localized area of suspected involvement; an unbundled rule to determine if separate bills were submitted for bundled services; a multidisciplinary rule to determine if different medical specialties are located at a sole facility, and billing unnecessary diagnostic procedures; a provider referral rule to determine if the referral source has financial ownership; an interpretation rule to determine if an additional charge for interpreting diagnostic results previously incorporated with fees for the diagnostic test is warranted; a timing rule to determine if the time between a diagnostic test and interpretation of the results indicates the diagnostic test or procedure was unnecessary. A processing means is coupled to the storage means for comparing the source data to the set of rules in the memory means. If the source data violates the set of rules, the relevant portion of the source data is identified and flagged as potentially fraudulent data. The flagged data can then be forwarded to a special investigator for a comprehensive analysis. The fraudulent data is transformed to graphs and charts so that the fraud is easily detected and identified.

Raw data such as accident reports, hospital reports, medical records, medicolegal documents, and all billing including, but not limited to, the Universal Claim Form—HCFA/CMS-1500 and UB-92/UB-04 claim forms, or their equivalent, superbills, ledgers, invoices, etc., are scanned and input to the system in a precise method as source data. The source data is mined via a maximum-security link over the Internet, or input by hand by specified individuals with Quality Assurance ("QA") provided to insure a zero factor error rate. Information regarding what type of document comprises the source data is entered and retained in the system for identification with specific sorting capabilities.

The present invention does not limit the amount or type/format of information that can be entered as source data. Information entered can be anything from photographs, diagnostic imaging/films to lab reports, ledgers, legal documents to handwritten doctor's notes and sticky post notes. All source data is scanned, and bate stamped when applicable, for later sorting and analysis. Optical character recognition ("OCR") capabilities are utilized within the present invention.

An advantage of the present invention is that after source data is entered, it is processed through an audit module, which analyzes and compares source data for billing and coding irregularities based on the set of user-defined rules. The present invention utilizes extensive intelligence procedures to compare source data and identify indicators of fraud found within the coding/billing and documentation process. These indicators of fraud, or "red flags", support claims management, agents, and counsel to detect and prevent fraud.

Another advantage of the present invention is that it can generate easy to read reports. These easy to read and understand reports enable a less skilled person to effectively and proficiently review the medical files for irregularities and visualize the potential fraud. Utilizing the present system provides an efficient, paperless environment to review/examine the source data without altering the integrity of the original documentation. Additionally, the detailed reports provide clarity, preciseness, and accuracy in the demonstration of abusive behavior when presented in trial testimony. These reports and color-coded graphs serve as visual exhibits at trial to illustrate where healthcare abuse and/or fraud is being committed for those who are generally not experienced in the medical arena.

Another advantage of the present invention is that it can contain an available library of inspection tools designed to assist government officials, claims management, SIU agents, and counsel with their investigation into the case or cases. These inspection tools can include, but are not limited to, instructions on the proper use of medical equipment utilized in diagnostic testing and/or treatment, clinic inspection techniques and diagnostic procedure protocols, manufacturer specification of diagnostic equipment, appropriate medical record keeping requirements and definitions of commonly used acronyms, definitions of HCPCS/CPT® and ICD-9/10 codes, rules and guidelines of medical billing procedures and protocols.

Yet another advantage of the present invention is the ability to duplicate and output data for use under an Independent Medical Examination (IME) and Peer Review. The IME/Peer Review component of the present invention organizes the source data into an overview window, a scheduling window, IME appointments window, IME/Peer Review physician's window, patient information window, IME/Peer Review report storage, letters log, and letter editor. This embodiment of the invention allows for additional input as an IME/Peer Review case progress to aid with organization and record keeping. A particular advantage to this embodiment includes the ability to automatically create and print IME/Peer Review request form letters to counsel, claimants/patients, physicians, and insurers.

It is therefore a primary object of the invention to provide a method and system that enables an investigator to analyze data and to detect fraud much faster, saving time and money for Insurance Companies, SIU Agents, Federal Agencies, Claims Management, Adjustors, and State Departments (i.e. Department Of Health).

Another important object of the present invention is to provide a method that generates reports that are flexible so that it can be provided to an expert witness for evaluation or sent to attorney or insurance carrier without the risk of disclosing unnecessary, privileged or confidential information and assuring compliance with HIPAA regulations.

Another important object of the present invention is to provide a method and system that reduces labor-intensive responsibilities and lowers overall expenses of analyzing data but maintains quality assurance capabilities.

Another important object of the present invention is to provide a method and system that has the ability to analyze the data across multiple healthcare providers, Place Of Service (POS), Ambulatory Surgical Centers (ASC), hospitals, tax identification numbers (TIN), patient/claimants, occurrences, procedures, disease/conditions, dates of service (DOS) and charges.

Another important object of the present invention is to provide a method and system that has the ability to analyze patterns within the data and to generate user-friendly reports and color-coded graphs/charts.

Another important object of the present invention is to provide a method and system that allows a user to define rules that generate an alert or flag contemporaneously with the analyzation of the data when the data being analyzed meets the user-defined rules.

Another important object of the present invention is to provide a method and system that is adaptable to a user's specialized areas of interest for specific investigative projects.

Another important object of the present invention is to provide a method and system with a user reference library on instructions of published protocols regarding the proper use of medical equipment, clinic inspection techniques, manufacturer specs of diagnostic equipment, required OIG Physician Compliance Program information, appropriate medical record keeping requirements, definitions of HCPCS/CPT® and ICD-9/10 codes, which are relevant to the data analyzation and fraud detection.

Another important object of the present invention is to provide a method and system that is flexible to adapt to meet healthcare providers, insurers, legal counsel, SIU and Federal Government needs in terms of generating output, access, flags, patterning and search criteria.

These and other important objects, advantages, and features of the invention will become clear as this description proceeds.

The present invention, accordingly, comprises the features of construction, combination of elements, and arrangement of parts that will be exemplified in the description set forth hereinafter and the scope of the invention will be indicated in the claims.

To the accomplishment of the foregoing and related ends, one or more embodiments comprise the features hereinafter fully described and particularly pointed out in the claims. The following description and the annexed drawings set forth, in detail, certain illustrative aspects and are indicative of but a few of the various ways in which the principles of the embodiments may be employed. Other advantages and novel features will become apparent from the following detailed description when considered in conjunction with the drawings and the disclosed embodiments are intended to include all such aspects and their equivalents.

V. BRIEF DESCRIPTION OF THE DRAWINGS

FIGS. 4a-14c are illustrations of various example reports and screen shots that can be generated according to various embodiments of a system and method for detecting healthcare insurance fraud;

FIG. 15 is a block diagram of a particular embodiment of a method to detect concealed objects using a handheld thermal imager;

VI. DETAILED DESCRIPTION

The word "exemplary" is used herein to mean "serving as an example, instance, or illustration." Any embodiment or design described herein as "exemplary" is not necessarily to be construed as preferred or advantageous over other embodiments or designs.

Figure 1:
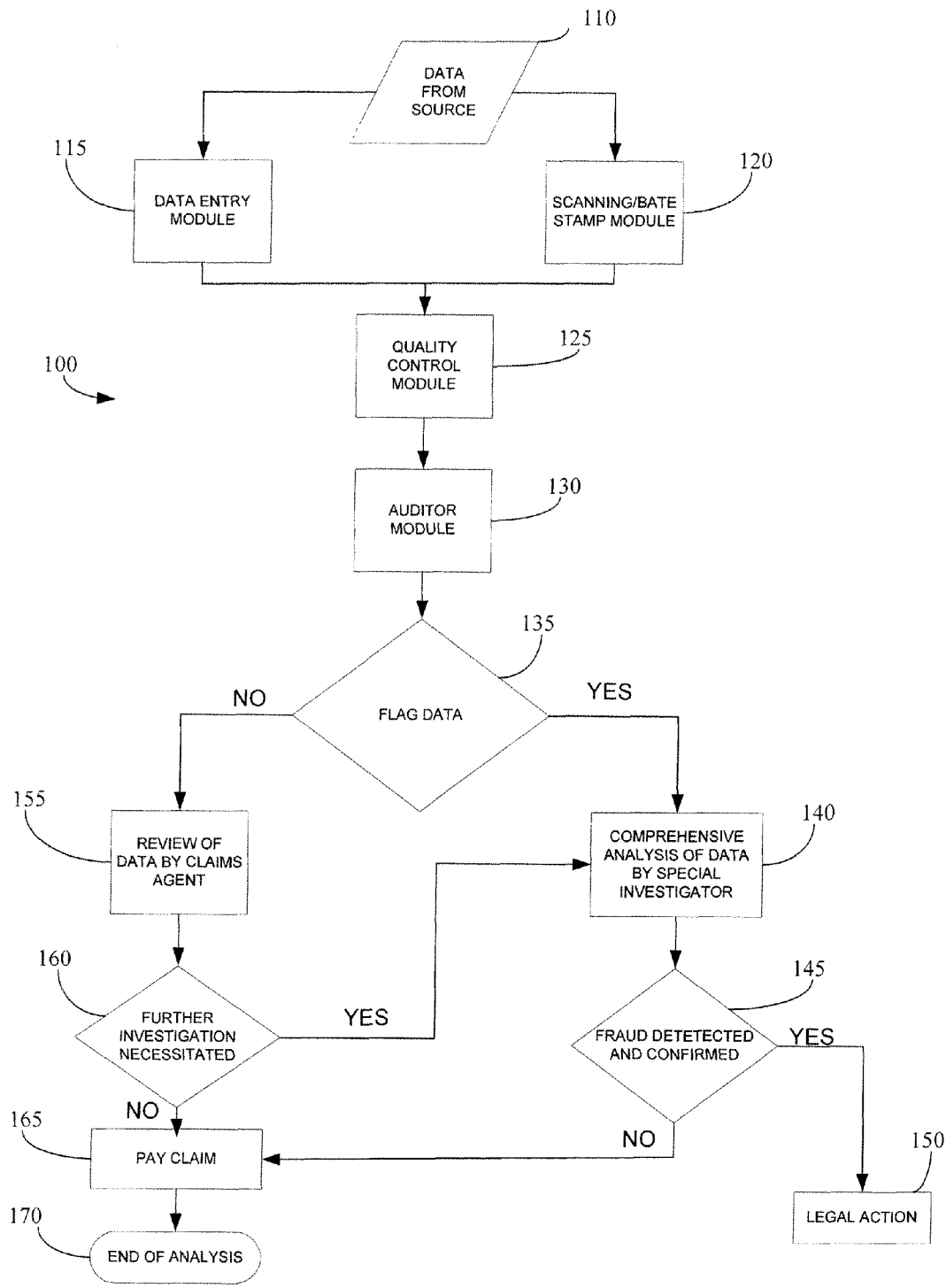
FIG. 1 is a flow diagram of a particular illustrative embodiment of a method and system for detecting healthcare billing and insurance fraud.

FIG. 1 is a flow diagram illustrating a method for detecting healthcare insurance fraud. Source data 110 is provided from various forms such as HCFA/CMS (1500), UB-92/UB-04 (1450), accident reports, emergency transportation forms, superbills/travel sheets, ledgers, invoices, EOBs, etc. The hard copy of the documents that comprise the source data 110 is captured by scanning module 120 and preferably stored digitally. The pertinent information from the source data 110 is also entered using data entry module 115. The next step in the fraud detection method is to validate the accuracy of the data entered via data entry module 115 using quality control module 125. Quality control module 125 crosschecks the data entered into the system with the digital image either of the document or the actual hard copy. Often times it is more convenient to crosscheck against a digital image rather than having to store and transport thousands of hard copies of source data 110.

Auditor module 130 includes a set of rules for comparing to source data 110 will detect indicators of fraudulent activity when the data violates the required pre-determined set of rules. The data is flagged 135 for further comprehensive analysis by a special investigator 140 if indicators of fraud are detected. If no data is flagged so that no indicators of fraud were detected then the data is forwarded to a claims agent for review 155.

The set of rules employed by auditor module 130 are comprised of algorithms that analyze data for specific indicators of fraud. An example of an indicator of fraud included in the set of rules of auditor module 130 is the lack of the adequate required history, examination and medical decision making by a doctor when billing high-level evaluation and management procedures and ordering or performing diagnostic tests. This includes performance of EMG and nerve conduction studies without the claimant having had full neurological examination of motor, sensory or reflex function. It also includes visual evoked potentials ("VEP") without the doctor having first performed visual acuity testing. Another example is performance of a brainstem auditory evoked response ("BAER") without the doctor having first evaluated cranial nerve functions or determined the thresholds of hearing. In addition, it is necessary to identify whether the claimant was on pain medication (i.e., Lortab, Vicodin, Lorcet, etc.) when these diagnostic tests were performed as the pain medication could significantly distort the results. Ordering or performing diagnostic imaging procedures without any clinical findings or justification of their performance.

Another indicator of potential fraud included in the set of rules of auditor module 130 is detecting a large number of diagnostic tests ordered at once. Diagnostic tests should be done to confirm suspected diagnosis. Therefore, the diagnostic test should be ordered within areas of symptoms and possible findings on examination. It is not appropriate to order numerous diagnostic tests to look at the entire body without any correlation to the history and examination or the localized areas of suspected involvement.

Yet another indicator of fraud is the unbundling of services. History and examination that includes a charge for the history and examination as well as additional charges for muscle testing, range of motion testing, cognitive testing and interpretation. All of these additional services should be included within the fee for the doctor's history and examination. They are not justified as separate bills and are detected by auditor module 130 as an indication of fraud.

Facilities that employ multiple types of medical specialties (i.e., chiropractic, orthopedic, physical therapy, massage therapy, neurology) all under the same roof are susceptible to fraudulent practices. These types of facilities ultimately have a higher percentage of referrals along with numerous diagnostic procedures and physical therapy modalities. Within the same facilities, some of the disciplines bill under a street address while other disciplines bill from a PO Box. Prior art audit systems do not have the ability to catch this type of abuse, multiple high complexity E&M consult codes and other CPT® codes are paid without review. However, auditor module 130 of the present invention analyzes tax identification numbers of each medical specialist to detect this type of fraudulent activity.

An additional charge for interpretation of diagnostic tests is another indicator of potential fraud. These additional charges should be included within the fees for the diagnostic tests when no modifier (e.g., "TC") is added to the CPT® code to indicate that this procedure is being billed for only the technical component. This would then reduce the fee for the diagnostic test. Any additional charges from the interpreting doctor should have a modifier by the same CPT® code to indicate only the interpretation of the diagnostic test. The total costs of the bill for the technical aspect of the diagnostic test and the interpretation of the results of the diagnostic test would then equal the UCR/RBRVS of that specific CPT® code. Accordingly, auditor module 130 flags data that identifies inconsistency related to this fraudulent activity.

Another indicator of potential fraud that auditor module 130 detects is the problem in the timing of certain medical procedures. This includes the performance of some tests too early (e.g., needle EMG performed, less than three weeks post injury), as well as long intervals between the order of diagnostic tests and the performance of the tests. There is significant cause to question the medical necessity of a diagnostic test when it is performed but not interpreted until weeks or months later. Another indicator is when an electrodiagnostic tests are scheduled and/or performed with a long interval of time between the comprehensive neurological history and examination. EMG and nerve conduction studies (as well as somatosensory evoked potentials ("SSEPs") are extensions of the neurological examination. There should be evidence of an updated thorough neurological examination not too long before the performance of the EMG and nerve conduction study or somatosensory evoked potential. Accordingly, auditor module 130 flags data related to this type of timing discrepancy.

Boilerplate type form letters of necessity are another indicator of potential fraudulent activity. Often printed years prior are form letters stating the need and medical necessity of the diagnostic testing/procedure to be performed and not referring or relating to the claimant in question. Generic letters of necessity are not adequate and do not address a specific claimant's problems or reasons for testing.

Diagnostic procedures billed with a CPT® code ending with 99 (i.e., "95999", "76499", etc.) are also problematic because this indicated the procedure performed is unlisted and prior art audit systems do not identify this resulting in a payment without inquiring about the procedure. When questioned or investigated, a typical response is "computer generated billing errors." In any event, auditor module 130 flags this data for further comprehensive review 140 to determine whether it is in fact a computer error or fraud.

Secured Audit module 130 resides on a computer that may be configured in a number of different forms for accepting input, processing the input according to specified instructions, and outputting the processing results, as is well known in the art. The computer may be, for example, a personal computer, a workstation, a supercomputer, a mainframe computer, a minicomputer, a handheld computer, a wearable computing device, a personal digital assistant ("PDA"), a smart appliance in the home, and so forth. By way of example, the computer may function as a server in the client/server architecture in a networking environment; alternatively, the computer may be a client device in the client/server architecture, a device operating within another networking environment, or a stand-alone device not operating within a networking environment. In accordance with the preferred embodiment of the present invention, audit module 130 includes a processing means comprising a central processing unit ("CPU"). The CPU is preferably one of the Intel families of microprocessors, one of the Advanced Micro Devices, Inc. families of microprocessors, one of the Motorola families of microprocessors, or one of the various versions of a Reduced Instruction Set ("RISC") microprocessor such as the PowerPC® chip manufactured by IBM.

Audit module 130 includes a memory means comprising random access memory ("RAM") and read-only memory ("ROM"). In preferred embodiments, ROM stores various controlling programs and RAM is preferably used for loading an operating system and selectively loading controlling programs and/or application programs.

As indicated in FIG. 1, if no fraud indicators are identified by auditor module 130, the data is passed along to the claims agent for review 155. The claims agent reviews the data and determines the next necessary action 160 to pay the claim 165, order a peer review and/or baseline IME, or authorize a comprehensive analysis of the data by a special investigator 140. As part of the comprehensive analysis by the special investigator 140, the investigator follows up or carries out inspections, surveillance, and/or runs data patterning algorithms to detect fraudulent activity and generate user-friendly reports and graphs to illustrate the fraud. If fraud is in fact identified 145, then legal action 150 or other appropriate action can be taken with the evidence of the fraud clearly identified. Otherwise, if no fraud is discovered after a comprehensive analysis 145, the claim is paid 165 and the analysis completed 170.

Figure 2:
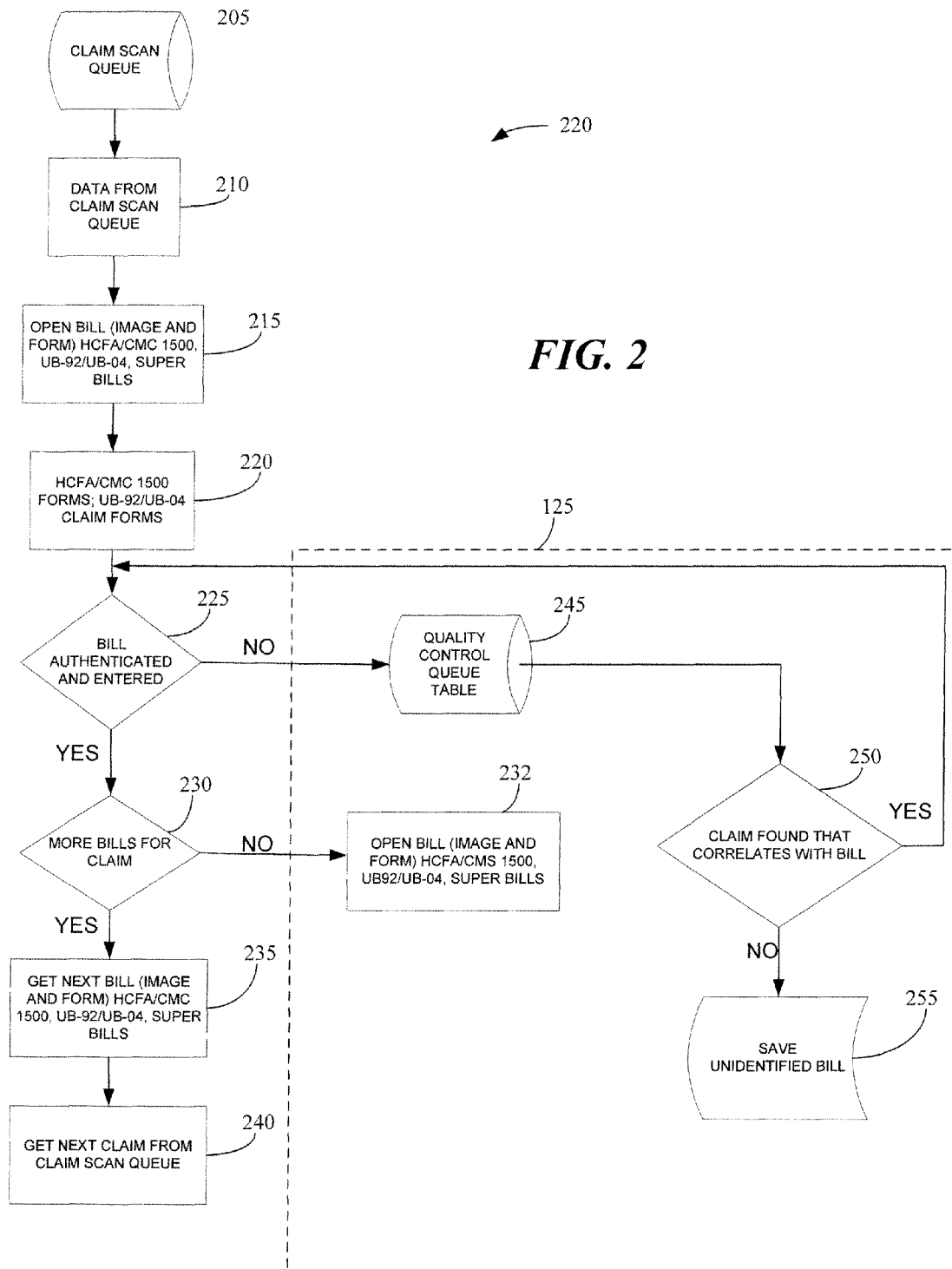
FIG. 2 is a flow diagram of a data entry and quality control system of a particular embodiment of the method and system for detecting healthcare insurance fraud.

Referring now to FIG. 2 illustrates the data entry module 115 and quality control module 125 of the present invention. Data that has been scanned is first stored in a claim scan queue 205. The storage means of claim scan queue may be one or more fixed or removable computer-readable media that is electrically, magnetically, optically, chemically, or otherwise altered to store computer-readable program code, where this media is readable by a device such as disk drive. In other embodiments claim scan queue 205 may be one or more other computer-readable media, such as a CD-ROM disk. Alternatively, claim scan queue 205 or portions thereof may be downloaded to RAM via a network. In other embodiments of claim scan queue 205, claim scan queue 205 can be partially or fully implemented with digital circuitry, analog circuitry, or a combination thereof.

Next, data from a desired claim is accessed from the claim scan queue 210. The data includes the National Standardized Claim Forms (HCFA/CMS-1500, UB-92/UB-04), Super Bills, and Ledgers among other types of various data. The electronically stored image is opened 215 and can be viewed by the user including the HCFA/CMS forms 220. The bill is then authenticated and entered 225. If the bill is not authenticated and entered it is processed by a quality control queue table 245 to determine the origin of the bill and/or to address the reason why the bill could not be authenticated. If the claim that correlates with the bill is found 250 or the issue is otherwise resolved, the bill is returned to be authenticated an entered 225. Conversely, if the bill cannot be correlated to a claim, then the bill is stored and isolated 255. The data entry module 115 determines whether there are any additional bills for the claim 230 so that it can retrieve the additional bills 235 for authentication and entry 225 until all the bills for that claim have been processed. Once all the bills for the claim have been processed, the data entered into the system 100 is manually checked 232 to verify the accuracy of the data entry.

Figure 3:
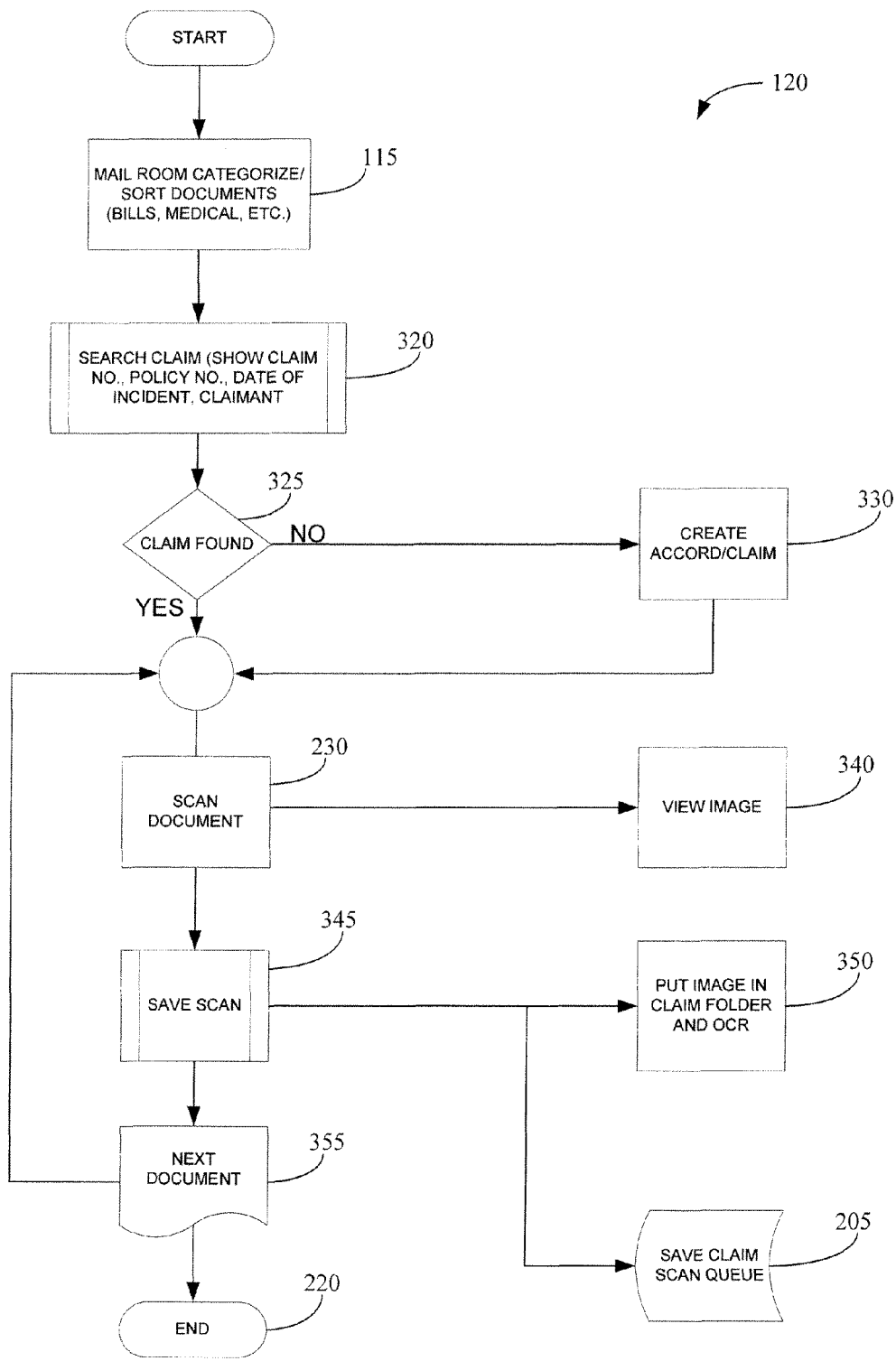
FIG. 3 is a flow diagram of a scanning system of a particular embodiment of a method and system for detecting healthcare insurance fraud.
Figure 4A:

As shown in FIG. 3, the scanning module 120 begins with the collection of the various documents 315 that comprise source data 110 for system 100. The next step is to search system 100 to determine whether a claim exists 320. If a claim is found 325, then the document is scanned 335 and saved to storage 345. This includes saving the image in the claim's folder 350 and to the claim scan queue 205. This process is repeated until all source data 110 has been scanned and saved to storage. The image can be viewed 340 prior to saving for quality control purposes. Alternatively, if a pre-existing claim is not found 325, then a claim file is first created 330 and the document is then scanned 335 and saved to storage 345.

Referring now to FIGS. 4a-14, is partial records and reports generated from test data for a claim reimbursement submitted to a healthcare insurer. FIGS. 4a-14 illustrates an example of the method and system for detecting healthcare insurance fraud. FIGS. 4a-4d show, among other things, particular CPT® codes that were entered for a patient on a series of different days. On each line item, the charge is indicated related to a particular HCPCS/CPT® code. In addition, the treating physician is identified, along with a name of the treating facility, billing entity, tax identification number and a referring source.

FIG. 5a shows a graphical representation of a series of selected CPT® codes based on the number of times that CPT® code was entered and is illustrated as a bar chart. FIG. 5a illustrates in a pie chart the value of particular CPT® codes relative to other CPT® codes for this particular claim. FIG. 5b is a written description of the CPT® codes that were used in this claim.

FIG. 6a further categorizes in a pie chart the CPT® codes and cumulative money total for expenses billed for surgery, medicine, radiology, evaluation and management, and others. FIG. 6b is a written description of each of those items illustrated in FIG. 6a.

Figure 7A:
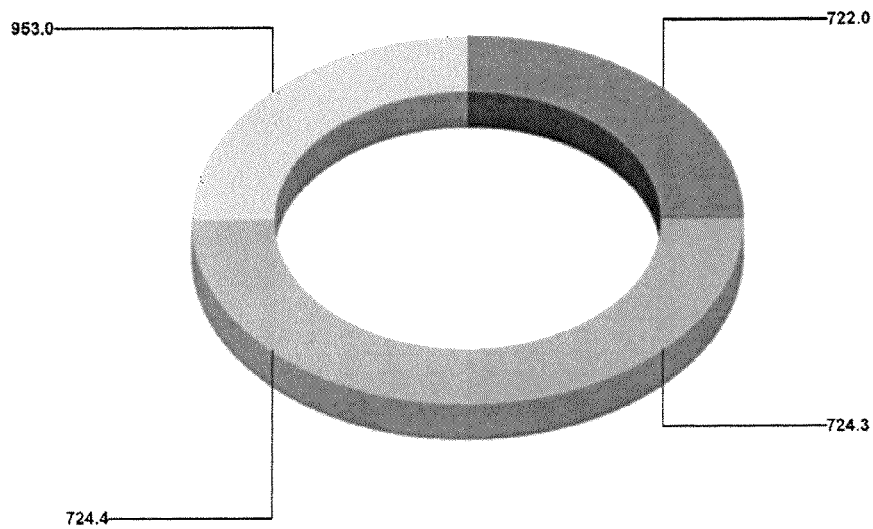
Figure 7B:
Figure 8D:

Referring now to FIG. 7a, the diagnosis codes (ICD-9/ICD-10) submitted with the claim is illustrated in a chart as percentages and FIG. 7b is a written description of the diagnosis codes. FIGS. 8a-8d is a report that identifies categorizes all charges submitted for particular providers.

Figure 10A:
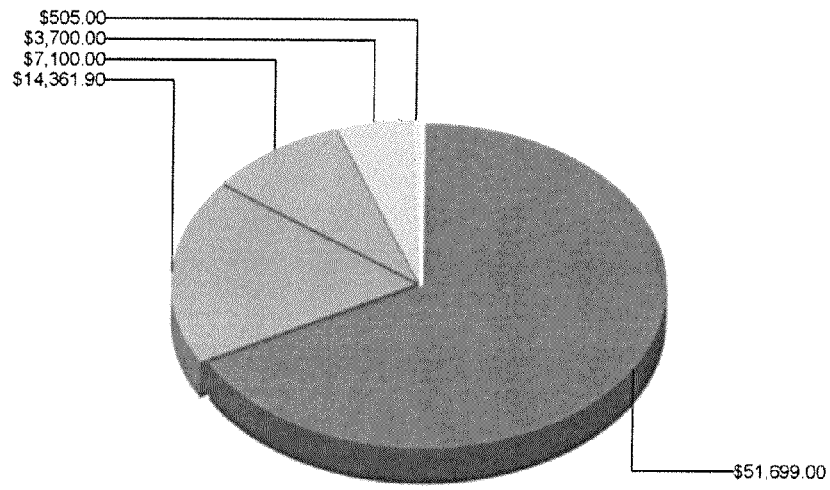
Figure 10B:

FIGS. 9a-9d shows the relative value units and different values assigned for particular procedures. FIG. 10a shows a chart illustrating how much each provider billed under this particular claim. In this example claim, Provider 2 billed $51,699.00 out of a total of $77,365.90. FIG. 10b is a report that shows the dates of service for each provider and also the number of bills submitted for each provider. FIG. 11a illustrates a cumulative money amount billed for surgery, medicine, radiology, evaluation and management, and others. FIG. 11b is report of those categories of services illustrated in FIG. 11a, organized by provider and associated amounts billed.

FIG. 12 illustrates automated generated statements of suspected fraudulent data. For example, under Provider 1, the automated generated statement of "CPT® code 62290 activities are included in the CPT® code 62287." This allows an investigator to quickly and efficiently identify unbundling and precisely what the issue is related to the claim for reimbursement. In this particular example, the method and system for detecting healthcare insurance fraud has automatically identified $24,635.00 in suspected unbundling patterns or fraudulent billing.

FIG. 13 illustrates automated red flags generated by the method and system for detecting healthcare insurance fraud. For example, the first red flag for Provider 1 states "Consultation CPT® Code 99243 is utilized without providing the name of the referring physician" which is one of the requirements in order to bill for a consult procedure.

Figure 14A:
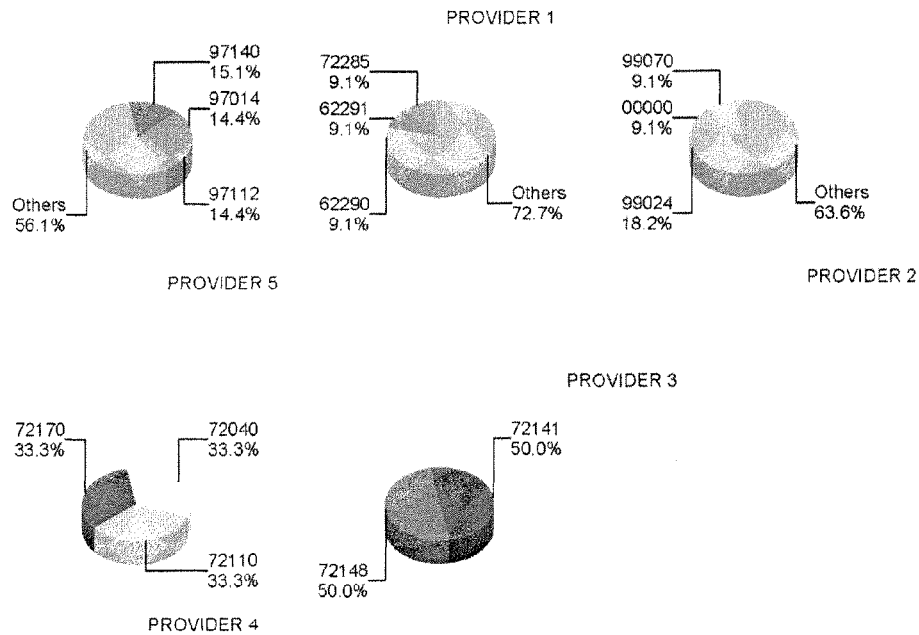

FIG. 14a shows pie charts that were developed based on the CPT® codes with the highest amounts charged for each provider. FIGS. 14b-14c is a report of those CPT® codes and amounts billed there under.

A flow diagram of a particular embodiment of the method for detecting healthcare insurance fraud is described in FIG. 15 and generally designated 400. At 402, a database containing source data related to a healthcare claim using a scanning module is created. Moving to 404, data from the database is selected to compare to a set of rules using an audit module. The selected data is compared, at 406, using the audit module. At 408, the audit module is used to identify fraudulent data from the selected data when the selected data violates at least one rule of the set of rules. The audit module is used to flag the fraudulent data, at 410, for comprehensive analysis by a special investigator. The audit module is used to generate a report illustrating patterns of irregularities within the source data to visually identify the fraudulent data displayed within the source data by user friendly graphs and charts, at 412. At least one automated statement, at 414, is generated for display to identify at least one rule that was violated by the selected data or to identify missing, inappropriate or improper documentation.

Figure 16:
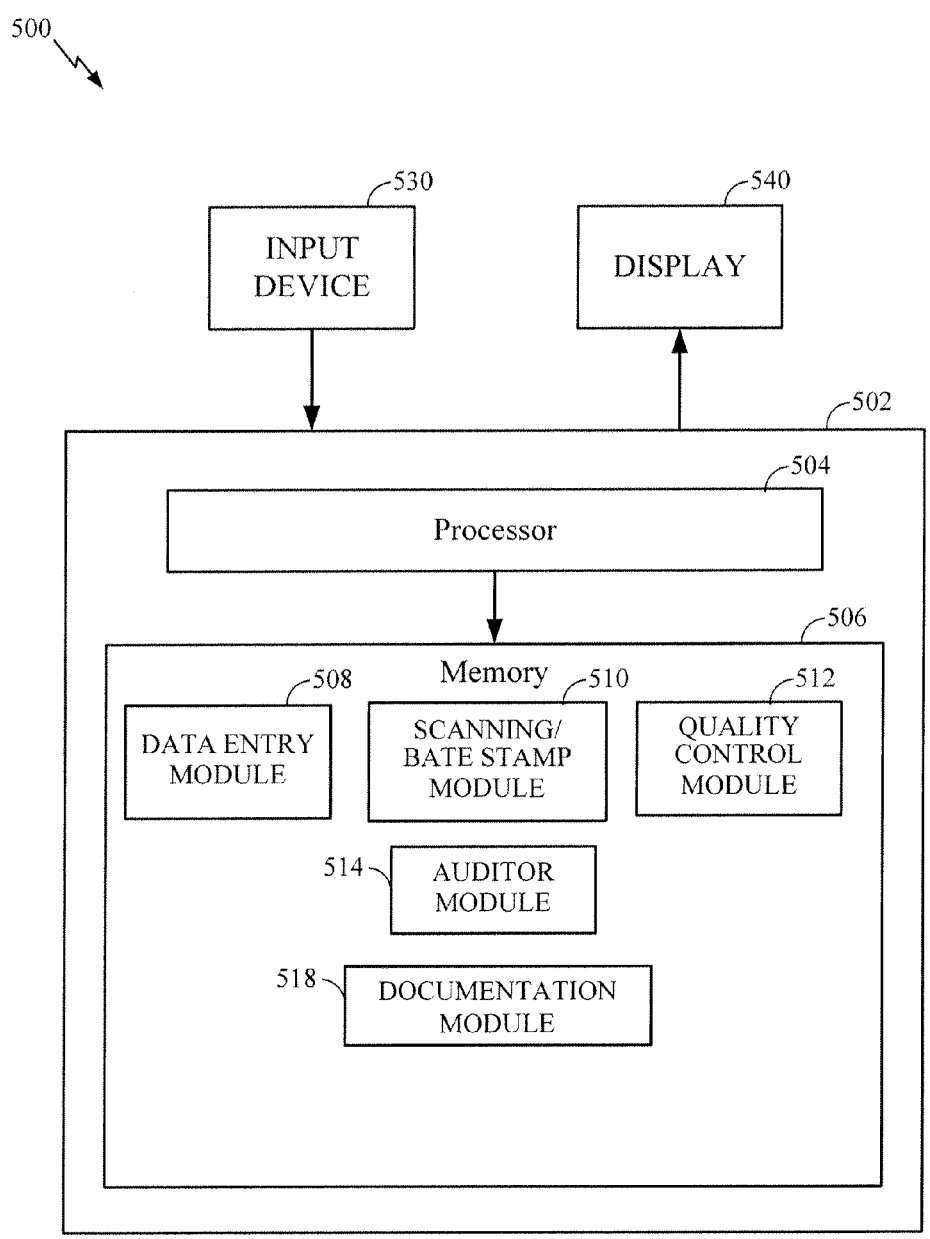
FIG. 16 is a block diagram of a particular illustrative embodiment of a system to detect concealed objects using a handheld thermal imager.

Referring to FIG. 16, a particular illustrative embodiment of the system for detecting healthcare insurance fraud is depicted and generally designated 500. In a particular embodiment, the system 500 may be a physical tool configured to perform the methods depicted in FIGS. 1-3 and 15. The system 500 includes a device 502 having at least one processor 504 and a memory 506 that is accessible to the processor 504. The memory 506 includes media that is readable by the processor 504 and that stores data and program instructions that are executable by the processor 504. The memory 506 may include several modules such as a data entry module 504, a scanning/Bate stamp module 510, a quality control module 512, an auditor module 514, and a documentation module 518. For example, the data entry module 508 may be used to enter pertinent information from the source data. A scanning/Bate stamp module 510 may be used to capture hard copies of various forms such as HCFA/CMS (1500), UB-92/UB-04 (1450), accident reports, emergency transportation forms, superbills/travel sheets, ledgers, EOBs, etc. A quality control module 514 may be used cross-check the data entered into the system with either the digital image of the document or the actual hard copy. The auditor module 514 may include a set of rules for comparing to source data 110 to detect indicators of fraudulent activity when the data violates the pre-determined set of rules. The data is flagged for further comprehensive analysis if indicators of fraud are detected. If no data is flagged so that no indicators of fraud were detected then the data is forwarded to a claims agent for review.

As an example of the audit module 514, generally there are two primary elements in the total cost of performing a surgical procedure. CPT®/HCPCS Codes are submitted/billed for services furnished by an ASC facility, where the procedure is performed, and are paid according to "Ambulatory Payment Classifications" (APCs) groups in conjunction with the Outpatient Prospective Payment System (OPPS). CPT®/HCPCS Codes submitted/billed for procedures furnished by the physician are costs of the physician's professional services for performing the procedure. The professional fee is paid to the physician; the facility fee is paid to the ASC. Physician coding and ASC coding of the procedures should match. If the audit module 514 determines that they do not match, the audit module 514 will flag the data and the documentation module 518, described below, may automatically generate a statement regarding the suspected fraudulent data.

Another example of the audit module 514 relates to revenue codes (payable) applied for each procedure. Relative Value Units (RVUs) are a way for hospitals and physician groups to calculate compensation for staff by using a set formula tied to various physician services. Revenue codes are three digit codes that affect reimbursement and represent the services provided by the ASC facility for a payer. Revenue codes go along with procedure (HCPCS/CPT®) codes. The use of revenue codes allows hospitals and ASC's (i.e., ASC Payment Rate) to use the same CPT® code in multiple departments because it will show which department the services were provided in or what type of item a patient might have received. A medical claim should not be paid if this is missing from a bill. If the audit module 514 determines that this information is missing, the audit module 514 will flag the data and the documentation module 518, described below, may automatically generate a statement regarding the missing revenue codes.

The documentation module 518 may be used for generating at least one automated statement for display to identify the at least one rule of the set of rules that was violated by the selected data using a documentation module. The documentation module is import to determine additional areas of concern. Documentation is the cornerstone of the quality of patient care in medicine. While documentation is extremely important for billing and coding, its primary purpose is to assist healthcare professional in providing appropriate services to patients. Thus, the documentation in each physician's office medical records, hospital settings, or ambulatory surgery centers, and rehabilitation centers and other settings must be accurate, complete, and reflect all of the services billed for each particular patient encounter.

An example of an automated statement that may be generated by the documentation module is "Documentation does not support the billed level of Evaluation and Management procedure." This medical necessity of a service is the overarching criterion for payment in addition to the individual requirements of a CPT® code. It would not be medically necessary or appropriate to bill a higher level of evaluation and management service when a lower service is documented and reasonable.

Another example of an automated statement that may be generated is "Inappropriate billing for nonphysician practitioner services under the physician's provider number on the CMS-1500 claim form." Services provided by nonphysician practitioners are to be reported/billed as "incident to" the supervising physician's service provided by nonphysician practitioner. Reimbursement is available for services provided by nonphysician practitioners who work in collaboration with a physician (e.g., M.D. or D.O.), which means that a written agreement is in place specifying the services to be provided by the nonphysician practitioner, who must work with one or more physicians to deliver health care services, receiving medical direction and appropriate supervision as required by state law.

Yet another example of an automated statement may be "ASC coding for anesthesiology services does not have the required documentation to support the medical necessity of the billed procedure(s)." Another example is "Inappropriate use of modifiers as documentation does not support the majority of the modified billed procedure codes." CPT® modifiers are reported on claims to provide clarification about procedures and services performed and the documentation must be provided to support their use. An automated statement may also relate to referrals such as "Disclosure and/or signed patient acknowledgment of facility referral ownership were not identified within the information provided for review." Another example is "CPT® code 01992 activities are included in the CPT® code 64490." Yet another example is "CPT® code 20999 is an Unlisted service or procedure. A special report describing nature, extent, need for the procedure, and the time, effort, equipment necessary to provide the service is required." The foregoing are all examples of automated statements that may be generated, but such examples are not intended to limit the scope of the method and system for detecting healthcare insurance fraud.

In addition, an input device 530 and a display 540 are coupled to the device 502. In a particular embodiment, the input device 530 may include a keyboard, a pointing device, a touch screen, a speech interface, another device to receive user input, or any combination thereof. A display 540 may be in direct communication with the processor 504, for displaying the graphs, charts and automated statements identifying the rules that were violated and also for identifying documentation that may be missing or not supportive of the healthcare claim submitted for reimbursement.

The modules 508, 510, 512, 514, and 518 may be implemented in hardware, firmware, software, other programmable logic, or any combination thereof. The memory 506 includes media that is readable by the processor 504 and that stores data and program instructions of the software modules 508, 510, 512, 514, and 518 that are executable by the processor 504. Additionally, the system 500 may include a display 540, for example, a cathode ray tube (CRT) display, liquid crystal display (LCD), light emitting diode (LED) display, plasma display, or other display device that is accessible to the processor 504.

Figure 17:
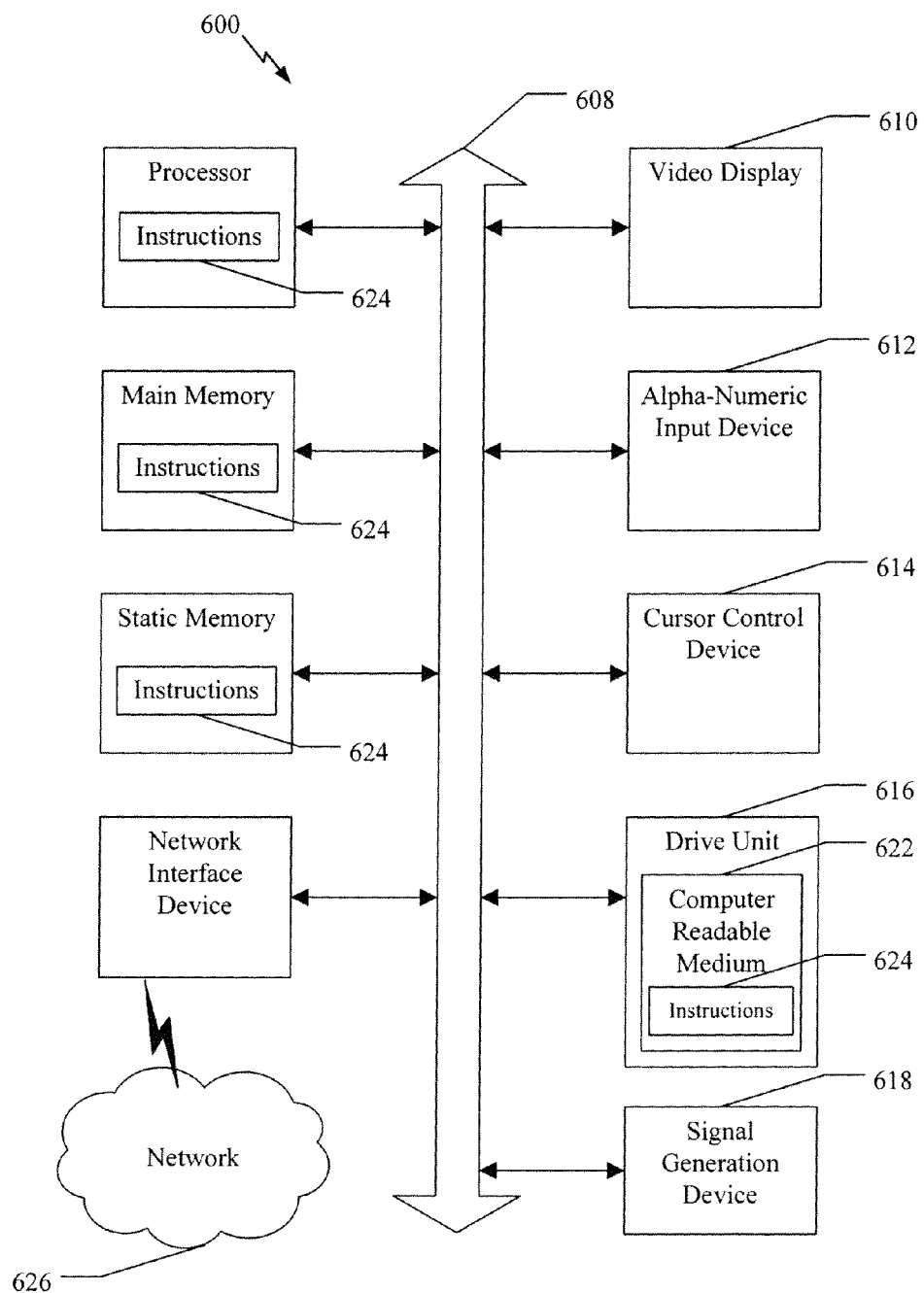
FIG. 17 is a block diagram of an illustrative embodiment of a general computer system.

Referring to FIG. 17, an illustrative embodiment of a general computer system is shown and is designated 600. The computer system 600 can include a set of instructions that can be executed to cause the computer system 600 to perform any one or more of the methods or computer based functions disclosed herein. The computer system 600, or any portion thereof, may operate as a standalone device or may be connected, e.g., using a network, to other computer systems or peripheral devices.

In a networked deployment, the computer system may operate in the capacity of a server, such as a video server or application server, or a media device. The computer system 600 can also be implemented as or incorporated into various devices, such as a personal computer (PC), a personal digital assistant (PDA), a mobile device, a palmtop computer, a laptop computer, a desktop computer, a communications device, a wireless telephone, a web appliance, a network router, switch or bridge, or any other machine capable of executing a set of instructions (sequential or otherwise) that specify actions to be taken by that machine. In a particular embodiment, the computer system 600 can be implemented using electronic devices that provide voice, video or data communication. Further, while a single computer system 600 is illustrated, the term "system" shall also be taken to include any collection of systems or sub-systems that individually or jointly execute a set, or multiple sets, of instructions to perform one or more computer functions.

As illustrated in FIG. 17, the computer system 600 may include a processor 602, e.g., a central processing unit (CPU), a graphics-processing unit (GPU), or both. Moreover, the computer system 600 can include a main memory 604 and a static memory 606 that can communicate with each other via a bus 608. As shown, the computer system 600 may further include a video display unit 610, such as a liquid crystal display (LCD), a flat panel display, a solid-state display, or a cathode ray tube (CRT). Additionally, the computer system 600 may include an input device 612, such as a keyboard, and a cursor control device 614, such as a mouse. The computer system 600 can also include a disk drive unit 616, a signal generation device 618, such as a speaker or remote control, and a network interface device 620.

In a particular embodiment, as depicted in FIG. 17, the disk drive unit 616 may include a computer-readable medium 622 in which one or more sets of instructions 624, e.g. software, can be embedded. Further, the instructions 624 may embody one or more of the methods or logic as described herein. In a particular embodiment, the instructions 624 may reside completely, or at least partially, within the main memory 604, the static memory 606, and/or within the processor 602 during execution by the computer system 600. The main memory 604 and the processor 602 also may include computer-readable media.

Those of skill would further appreciate that the various illustrative logical blocks, configurations, modules, circuits, and algorithm steps described in connection with the embodiments disclosed herein may be implemented as electronic hardware, computer software, or combinations of both. To clearly illustrate this interchangeability of hardware and software, various illustrative components, blocks, configurations, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The steps of a method or algorithm described in connection with the embodiments disclosed herein may be embodied directly in hardware, in a software module executed by a processor, or in a combination of the two. A software module may reside in random access memory (RAM), flash memory, read-only memory (ROM), programmable read-only memory (PROM), erasable programmable read-only memory (EPROM), electrically erasable programmable read-only memory (EEPROM), registers, hard disk, a removable disk, a compact disc read-only memory (CD-ROM), or any other form of storage medium known in the art. An exemplary storage medium is coupled to the processor such that the processor can read information from, and write information to, the storage medium. In the alternative, the storage medium may be integral to the processor. The processor and the storage medium may reside in an application-specific integrated circuit (ASIC). The ASIC may reside in a computing device or a user terminal. In the alternative, the processor and the storage medium may reside as discrete components in a computing device or user terminal.

The previous description of the disclosed embodiments is provided to enable any person skilled in the art to make or use the disclosed embodiments. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope possible consistent with the principles and novel features as defined herein.

Now that the invention has been described,
What is claimed is:

1. A method for detecting healthcare insurance fraud, the method comprising:
creating a data base containing source data related to at least one healthcare claim submitted for reimbursement;
selecting data from the data base to compare to a set of rules using an audit module;
comparing the selected data to the set of rules using the audit module, wherein the set of rules includes a history rule, quantity rule, unbundled rule, multidisciplinary rule, interpretation rule, timing rule, coding rule, or any combination thereof, for detecting and identifying fraud;
using the audit module to automatically identify suspected fraudulent data when the selected data violates at least one rule of the set of rules;
using the audit module to flag the fraudulent data;
using the audit module to generate a report illustrating patterns of irregularities within the source data to visually identify the fraudulent data displayed within the source data by user-friendly graphs and charts; and
generating at least one automated statement for display to identify the at least one rule of the set of rules that was violated by the selected data using a documentation module.

2. The method of claim 1, further comprising identifying selected data that does not support a billed level of evaluation and management procedures.

3. The method of claim 1, further comprising identifying selected data that reflects services provided by nonphysician practitioners submitted under a physician's provided number for reimbursement.

4. The method of claim 1, wherein the source data includes accident reports, hospital records and billing claim forms.

5. The method of claim 1, further comprises comparing the selected data to the history rule of the set of rules using the audit module when the selected data includes a bill for performing a diagnostic test.

6. The method of claim 1, further comprises comparing the selected data to the quantity rule of the set of rules using the audit module when the selected data includes a bill for performing a large quantity of diagnostic tests.

7. The method of claim 1, further comprises comparing the selected data to the unbundled rule of the set of rules using the audit module when the selected data includes a bill for history and examination of a claimant in addition to a battery of testing procedures.

8. The method of claim 1, further comprises comparing the selected data to the multidisciplinary rule of the set of rules using the audit module when the selected data includes a bill for different medical specialties arising from the same billing address or tax identification number.

9. The method of claim 1, further comprises comparing the selected data to the interpretation rule of the set of rules using the audit module when the selected data includes a bill for interpretation separate from the bill for performing a diagnostic test.

10. The method of claim 1, further comprises comparing the selected data to the timing rule of the set of rules using the audit module when the selected data includes a bill for a diagnostic test.

11. The method of claim 1, further comprises comparing the selected data to the coding rule of the set of rules when the selected data includes a bill with a billing code that does not correlate to a table of billing codes.

12. A computer program product for detecting and identifying fraud arising from a healthcare claim, the computer program product embodied on one or more non-transitory computer-readable media and comprising:
computer-readable program code means for storing a data base containing source data related to at least one healthcare claim submitted for reimbursement;
computer-readable program code means for storing a set of rules for detecting and identifying fraud related to the healthcare claim, wherein the set of rules includes a history rule, quantity rule, unbundled rule, multidisciplinary rule, interpretation rule, timing rule, coding rule, or any combination thereof, for detecting and identifying fraud;

computer-readable program code means for comparing the source data to the set of rules;

computer-readable program code means for identifying fraudulent data within the source data that violates at least one rule of the set of rules;

computer-readable program code means for flagging the fraudulent data;

computer-readable program code means for illustrating patterns of irregularities within the source data to visually identify the fraudulent data displayed within the source data by user-friendly graphs and charts; and computer-readable program code means for generating at least one automated statement for display to identify the at least one rule of the set of rules that was violated by the selected data.

* * * * *